US010905780B2

(12) United States Patent
Evans et al.

(10) Patent No.: US 10,905,780 B2
(45) Date of Patent: Feb. 2, 2021

(54) COMPOUNDS, SYSTEMS, AND METHODS FOR MONITORING AND TREATING A SURFACE OF A SUBJECT

(71) Applicant: THE GENERAL HOSPITAL CORPORATION, Boston, MA (US)

(72) Inventors: Conor L. Evans, Boston, MA (US); Gabriela Apiou, Boston, MA (US); Alexander J. Nichols, Boston, MA (US); Emmanouil Rousakis, Boston, MA (US); Zongxi Li, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 16/054,028

(22) Filed: Aug. 3, 2018

(65) Prior Publication Data

US 2018/0344878 A1    Dec. 6, 2018

Related U.S. Application Data

(62) Division of application No. 15/684,040, filed on Aug. 23, 2017, now Pat. No. 10,039,842, which is a division of application No. 14/903,710, filed as application No. PCT/US2014/042377 on Jun. 13, 2014, now Pat. No. 9,789,206.

(30) Foreign Application Priority Data

Jul. 10, 2013    (WO) ................ PCT/US2013/049847

(51) Int. Cl.
*C07D 487/22*    (2006.01)
*A61K 49/00*    (2006.01)
*A61B 5/00*    (2006.01)
*A61B 5/1455*    (2006.01)
*A61B 90/00*    (2016.01)
*A61F 13/00*    (2006.01)

(52) U.S. Cl.
CPC ...... *A61K 49/0015* (2013.01); *A61B 5/14551* (2013.01); *A61B 5/14552* (2013.01); *A61B 5/14556* (2013.01); *A61B 5/443* (2013.01); *A61B 5/6833* (2013.01); *A61B 90/39* (2016.02); *C07D 487/22* (2013.01); *A61B 5/0022* (2013.01); *A61B 5/4839* (2013.01); *A61B 5/743* (2013.01); *A61B 2562/12* (2013.01); *A61F 2013/0097* (2013.01)

(58) Field of Classification Search
CPC .................................................. C07D 487/22
See application file for complete search history.

(56) References Cited

U.S. PATENT DOCUMENTS

| 5,837,865 A | 11/1998 | Vinogradov et al. |
| 6,014,577 A | 1/2000 | Henning et al. |
| 6,207,461 B1 | 3/2001 | Baumann et al. |
| 6,362,175 B1 | 3/2002 | Vinogradov et al. |
| 6,664,111 B2 | 12/2003 | Bentsen et al. |
| 8,084,093 B2 | 12/2011 | Tanaka et al. |
| 9,650,566 B2 * | 5/2017 | Gamsey ............ A61K 49/0036 |
| 2002/0018843 A1 | 2/2002 | Van Antwerp et al. |
| 2003/0050543 A1 | 3/2003 | Hartmann |
| 2003/0203888 A1 | 10/2003 | Boyle et al. |
| 2006/0182738 A1 | 8/2006 | Holmes |
| 2012/0135973 A1 | 5/2012 | Salvemini et al. |
| 2013/0224874 A1 | 8/2013 | Vinogradov et al. |

FOREIGN PATENT DOCUMENTS

| JP | 2009162871 A | 7/2009 |
| WO | WO 88/09782 | * 12/1988 |
| WO | 2007050269 A2 | 5/2007 |
| WO | 2007081811 A2 | 7/2007 |
| WO | 2014011724 A1 | 1/2014 |

OTHER PUBLICATIONS

Unterlass et al. Chem.Commun., 2011, 47, 7057-7059.*
Babilas, et al., Transcutaneous pO2 Imaging During Tourniquet-Induced Forearm Ischemia Using Planar Optical Oxygen Sensors, Skin Research and Technology, 2008, 14:304-311.
Badocco, et al., Signal Drift of Oxygen Optical Sensors. Part I: Rationalization of the Drift Nature and Its Experimental Check with a Light Intensity Detection Based Sensor, Sensors and Actuators B, 2013, 181:943-948.
Bariya, et al., Microneedles: An Emerging Transdermal Drug Delivery System, Journal of Pharmacy and Pharmacology, 2012, 64:11-29.
Brantley, et al., Unclicking the Click: Mechanically Facilitated 1,3-Dipolar Cycloreversions, Science, 2011, 333 (6049):1606-1609.
Chen, et al., Facilitation of Transcutaneous Drug Delivery and Vaccine Immunization by a Safe Laser Technology, J. Control Release, 2012, 159(1):43-51.
Dougherty, et al., Photodynamic Therapy, Journal of the National Cancer Institute, 1998, 90(12):889-905.
Eaton, et al., Effect of Humidity on the Response Characteristics of Luminescent PtOEP Thin Film Optical Oxygen Sensors, Sensors and Actuators B, 2002, 82:94-104.

(Continued)

*Primary Examiner* — Brian E McDowell
(74) *Attorney, Agent, or Firm* — Quarles & Brady LLP

(57) ABSTRACT

Compounds, systems, and methods are provided for the design and assembly of a non-invasive, analyte sensing dressing. The dressing can be therapeutic. The dressing includes a sensor and a matrix. The sensor is capable of detecting analytes such as molecular oxygen, carbon dioxide, nitric oxides, dissolved analytes in plasma, and hydrogen ions. The matrix is at least partially permeable to the analyte. The device emits a detectable signal when the sensor is excited in the presence of the analyte. In one version of the dressing, the sensor includes a meso-unsubstituted metallated porphyrin that is sensitive towards oxygen. The metallated porphyrin can be excited when illuminated at a first wavelength, followed by emission of phosphorescence at a second wavelength whose intensity can be used as an indicator for oxygen concentration.

11 Claims, 18 Drawing Sheets

(56) References Cited

OTHER PUBLICATIONS

Filatov, et al., The Synthesis of New Tetrabenzo- and Tetranaphthoporphyrins Via the Addition Reactions of 4,7-dihydroisoindole, Tetrahedron, 2011, 67:3559-3566.
Finikova, et al., Porphyrin and Tetrabenzoporphyrin Dendrimers: Tunable Membrane-Impermeable Fluorescent pH Nanosensors, J. Am. Chem. Soc., 2003, 125:4882-4893.
Finikova, et al., Synthesis and Luminescence of Soluble meso-Unsubstituted Tetrabenzo- and Tetranaphthol[2,3]porphyrins, J. Org. Chem., 2005, 70:9562-9572.
Gethin, The Significance of Surface pH in Chronic Wounds, Wounds UK, 2007, 3(3):52-55.
Hirobe, et al., Clinical Study of Transcutaneous Vaccination Using a Hydrogel Patch for Tetanus and Diptheria, Vaccine, 2012, 30(10):1847-1854.
Hood, et al., The Effects of an Alpha Hydroxy Acid (Glycolic Acid) on Hairless Guinea Pig Skin Permeability, Food and Chemical Toxicology, 1999, 37(11):1105-1111.
Ito, et al., Synthesis of Benzoporphyrins Functionalized with Octaester Groups, Tetrahedron Letters, 2001, 42:45-47.
Jorgensen, et al., Pain and Quality of Life for Patients with Venous Leg Ulcers: Proof of Concept of the Efficacy of Biatain-Ibu, a New Pain Reducing Wound Dressing, Wound Repair and Regeneration, 2006, 14(3):233-239.
Kellner, et al., Determination of Oxygen Gradients in Engineered Tissue Using a Fluorescent Sensor, Biotechnol. Bioeng., 2002, 80:73-83.
Meier, et al., Simultaneous Photographing of Oxygen and pH In Vivo Using Sensor Films, Angew. Chem. Int. Ed., 2011, 50:10893-10896.
Orgill, Excision and Skin Grafting of Thermal Burns, New England Journal of Medicine, 2009, 360:893-901.
Park, et al., Complex Wounds and Their Management, Surg. Clin. N. Am., 2010, 90(6):1181-1194.
Prausnitz, et al., Transdermal Drug Delivery, Nat. Biotechnol., 2008, 26(11):1261-1268.
Snyder, Treatment of Nonhealing Ulcers with Allografts, Clinics in Dermatology, 2005, 23(4):388-395.
Ungerbock, et al., Microfluidic Oxygen Imaging Using Integrated Optical Sensor Layers and a Color Camera, Lab on a Chip, 2013, 13:1593-1601.
Vrdoljak, et al., Coated Microneedle Arrays for Transcutaneous Delivery of Live Virus Vaccines, Journal of Controlled Release, 2012, 159(1):34-42.
European Patent Office, Extended European Search Report, Application No. 13817635.9, dated Mar. 11, 2016.
PCT International Search Report and Written Opinion, PCT/US2013/049847, dated Oct. 31, 2013.
PCT International Search Report and Written Opinion, PCT/US2014/042377, dated Oct. 6, 2014.
Fuhrhop, et al., Hexadecahydro-29H,31H-tetrabenzo[b,g,l,q]porphin and -octayl Octaacetate, Liebigs Ann. Chem., 1985, pp. 689-695.
Hierlemann, et al., Effective Use of Molecular Recognition in Gas Sensing: Results from Acoustic Wave and in Situ FT-IR Measurements, Anal. Chem., 1999, 71(15):3022-3035.
Kopranenkov, et al., Synthesis and Electronic Absorption Spectra of Substituted Tetrabenzoporphins, Chemistry of Heterocyclic Compounds, 1988, 24(6):630-637 [Translated From Khimiya Geterotsiklicheskikh Soedinenii, 1988, 6:773-779].
Kopranenkov, et al., Synthesis and Electronic Absorption Spectra of Substituted Tetrabenzoporphins, Database CA [Online], Chemical Abstracts Service, XP002763725, Database Accession No. 1989:423266.
Tolbin, et al., Synthesis and Spectroscopic Properties of New Water-Soluble Phthalocyanines Containing Pyridinium Hydrochloride Fragments, Russian Chemical Bulletin, International Edition, 2007, 56(12):2433-2437.
European Patent Office, Extended European Search Report, EP 14822888.5, dated Nov. 15, 2016.
Machine translation of Japanese Patent Application No. 2009-162871.

\* cited by examiner

M: Pt, Pd

COMPOUNDS, SYSTEMS, AND METHODS FOR MONITORING AND TREATING A SURFACE OF A SUBJECT

CROSS-REFERENCES TO RELATED APPLICATIONS

This application is a divisional application of U.S. patent application Ser. No. 15/684,040 filed Aug. 23, 2017, which is a divisional application of U.S. patent application Ser. No. 14/903,710 filed Jan. 8, 2016, now U.S. Pat. No. 9,789,206, which is a 371 application of PCT/US2014/042377 filed Jun. 13, 2014, which claims priority from PCT International Application No. PCT/US2013/049847 filed Jul. 10, 2013.

STATEMENT REGARDING FEDERALLY SPONSORED RESEARCH

Not Applicable.

BACKGROUND OF THE INVENTION

1. Field of the Invention

The invention relates to compounds useful as sensors in a non-invasive, analyte sensing dressing. The compounds can be meso-unsubstituted metallated porphyrins that are sensitive towards oxygen. The metallated porphyrins can be excited when illuminated at a first wavelength, followed by emission of phosphorescence at a second wavelength whose emission intensity and/or lifetime can be used as an indicator for oxygen concentration.

2. Description of the Related Art

In a clinical setting, it is often desirable to monitor a patient's health by measuring tissue gas levels. Tissue-gas analyses are an essential part of modern patient care and are used in the diagnosis and treatment of a number of conditions. In particular, measurement of tissue oxygen concentration is heavily relied upon both for general monitoring of overall patient health and for treatment of specific conditions, such as ischemia, burns, and diabetic foot syndrome.

In general, there are three main technologies that are used to perform blood and tissue gas analyses. A first apparatus, known as a pulse oximeter, is a basic, non-invasive instrument that detects hemoglobin oxygen saturation. Measuring the percentage of oxygen-bound hemoglobin provides an estimate of arterial oxygenation. The device may be placed on a finger or another body part, and the measurement is accomplished by monitoring the reflectance or absorbance of incident light. While pulse oximetry is a fast and simple technique, the main drawback is that the measurement does not measure absolute arterial oxygen concentrations. In particular, an inaccurate diagnosis may arise is situations where hemoglobin concentrations are low or when hemoglobin is bound to a species other than oxygen.

A second, more direct measurement of tissue gas levels may be made using probe-based systems. Two existing methods based on transcutaneous oxygen ($TcpO_2$) measurement involve either electrodes or an optical sensor foil-based patch. As opposed to a pulse oximeter, $TcpO_2$ measurements can provide a direct indication of microvascular function as $TcpO_2$ measures the actual oxygen supply available for the skin tissue cells. $TcpO_2$ also responds to macrocirculatory events, such as a change in blood pressure.

For the more common electrode based system, the $TcpO_2$ monitor consists of a combined platinum and silver electrode covered by an oxygen-permeable hydrophobic membrane, with a reservoir of phosphate buffer and potassium chloride trapped inside the electrode. A small heating element is located inside the silver anode. In practice, the electrode is applied to an acceptable site on the skin and is heated to 44° C. in order to provide a measurement.

Another commercial system known as the VisiSens™ system combines optical sensor foils with imaging technology. Fluorescent chemical optical sensor foils are attached to the sample surface and read out non-invasively using a microscope. Two-dimensional visualization of oxygen, pH, or $CO_2$ distributions over time can be performed with microscopic resolution.

Limitations of $TcpO_2$ systems include the need for two-(or more) point calibrations with specially prepared, well-defined samples. The sensor must be in contact with the tissue through a contact liquid. If there is air between the tissue and the sensor, the values will be questionable. For commercial electrode systems, it may take 15-20 minutes after the probe has been placed on the skin for the $TcpO_2$ reading to stabilize and it is recommended that calibrations be performed prior to each monitoring period, when changing measuring sites, every four hours, and/or every time an electrode has been remembraned. In addition, heating may affect the ability to acquire physiologically relevant measurements.

A third approach to monitoring gas levels involves a blood test. The test is performed using a blood sample drawn from an artery. The machine used for analysis aspirates this blood from the syringe and measures the pH and the partial pressures of oxygen and carbon dioxide. The bicarbonate concentration can also be calculated. An advantage of the test is that results are usually available for interpretation within minutes. However, the test is invasive, requires a trained practitioner to accurately acquire a sample, and samples must be maintained at room temperature and analyzed quickly or results may be inaccurate.

Overall, while there exists a number of methods for monitoring tissue gas levels, each of these methods possesses inherent drawbacks. It would, therefore, be desirable to have a system and method for monitoring tissue gas levels that (i) is minimally or non-invasive, (ii) is capable of accurately measuring the actual oxygen supply, (iii) provides fast readout, and (iv) requires minimal expertise so as to enable to be administered by the patient or other nonpractitioner. In particular, there is a need for compounds that can be used as an oxygen sensor in a non-invasive, analyte sensing dressing.

SUMMARY OF THE INVENTION

The present invention overcomes the above and other drawbacks by providing compounds useful as an oxygen sensor in a non-invasive, analyte sensing dressing. The compounds can be meso-unsubstituted metallated porphyrins that are sensitive towards oxygen. The metallated porphyrins can be excited when illuminated at a first wavelength, followed by emission of phosphorescence at a second wavelength whose intensity or lifetime can be used as an indicator for oxygen concentration. A non-invasive, oxygen-sensing dressing including the compounds may be applied to the surface of tissues such as skin in order to provide fast, accurate readout without the requirement of specialized training.

In one aspect, the present invention provides an interactive, sensing, and therapeutic delivery device designed for the detection and monitoring of tissue properties that are used to inform a user of the specific need and spatial location for therapeutic intervention. In certain embodiments, the sensing and therapeutic delivery device can be triggered to spatially release therapeutics using an interacting portion. Following therapeutic release, the present invention can continue to monitor tissue properties in response to treatment.

In accordance with one aspect of the invention, a device is provided that includes a sensor configured to detect a concentration of an analyte that includes, but is not limited to molecular oxygen, carbon dioxide, nitric oxides, dissolved analytes in plasma, and hydrogen ions. Preferably, the analyte is oxygen. The device also includes a matrix compatible with the sensor, at least a portion of the matrix being accessible to and/or permeable to the analyte. The device includes a dressing comprising the matrix and a sensor including a compound of the present disclosure, wherein the device emits a signal, such as a phosphorescent signal, in response to the concentration of the analyte detected by the sensor including the compound of the present disclosure.

In accordance with another aspect of the invention, a method of manufacturing a device for detecting an analyte is provided that comprises selecting a sensor including a compound of the present disclosure. The sensor is configured to detect a concentration of an analyte including but not limited to molecular oxygen, carbon dioxide, nitric oxides, dissolved analytes in plasma or tissue, and hydrogen ions. Preferably, the analyte is oxygen. The method also includes selecting a compatible matrix based on a chemical nature of the sensor and enmeshing the sensor in the compatible matrix, at least a portion of the matrix being permeable to the analyte. The method further includes incorporating the matrix into a dressing, wherein the dressing is configured to emit a signal that varies in response to the concentration of the analyte detected by the sensor including the compound of the present disclosure.

In accordance with yet another aspect of the invention, a kit is provided for detecting an analyte. The kit includes a dressing comprising a sensor including a compound of the present disclosure. The sensor is configured to detect at least one analyte. The dressing includes a matrix compatible with the sensor and a detector configured to actuate the sensor and measure a signal as a function of a position on a surface of the dressing. The analyte may be, but is not limited to, molecular oxygen, carbon dioxide, nitric oxides, dissolved analytes in plasma, and hydrogen ions, and the signal corresponds to the presence of the analyte proximate to the surface of the dressing. Preferably, the analyte is oxygen.

In one form, the compounds of the present disclosure are phosphorescent compounds wherein the phosphorescence is quenched by oxygen. A phosphorescent portion of the compound can be converted to the excited triplet state by light absorption, followed by return to the ground state either with light emission (phosphorescence) or by energy transfer to molecular oxygen when oxygen molecules are present to collide with molecules of the phosphorescent compound in the excited triplet state. Therefore, increasing oxygen partial pressure causes an increase in the rate of decay of phosphorescence (shorter lifetimes) and a decrease in total phosphorescence intensity. The compound can be used with an oxygen measurement system including a light source, a camera, and a computer. The light source illuminates the compound such that a phosphorescent portion of the compound is converted to the excited triplet state. Light emission (phosphorescence) can be detected with the camera, and images from the camera can be placed in the computer memory (which may be, for example, in a mobile device, camera or smartphone) for calculation and construction of an oxygen pressure map from the data. U.S. Pat. No. 6,362,175 provides an example method for creating an oxygen pressure map using other phosphorescent compounds in which the phosphorescence is quenched by oxygen.

In one embodiment, the compound of the present disclosure is a phosphorescent meso-unsubstituted porphyrin having the Formula (I):

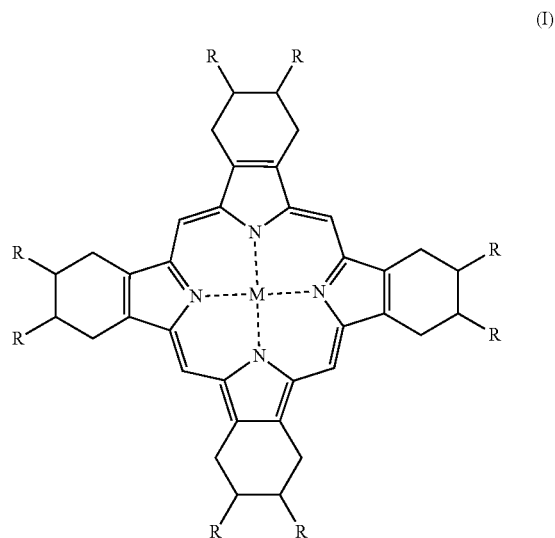

wherein M is a metal, wherein each R is independently an atom or a group of atoms, and wherein at least one R is —OR$^1$, wherein R$^1$ is an atom or a group of atoms.

In the porphyrin of Formula (I), R$^1$ may be selected from the group consisting of hydrogen, substituted or unsubstituted alkyl, substituted or unsubstituted alkyl carbonyl, substituted or unsubstituted alkenyl, substituted or unsubstituted alkynyl, substituted or unsubstituted cycloalkyl, substituted or unsubstituted heterocycloalkyl, substituted or unsubstituted aryl, heteroaryl, halo, cyano, and nitro. In one example of the porphyrin of Formula (I), R$^1$ is hydrogen. In another example of the porphyrin of Formula (I), R$^1$ is alkynyl, such as 2-propynyl (propargyl). In the porphyrin of Formula (I), a plurality of R can be —OR$^1$, and optionally, every R can be —OR$^1$.

In one example of the porphyrin of Formula (I), R$^1$ includes a triazolyl group. The triazolyl group may be bonded to O via an alkyl chain. In one example of the porphyrin of Formula (I), R$^1$ includes an alkylglutamate group. R$^1$ may terminate in a pair of alkylglutamate groups. In another example of the porphyrin of Formula (I), R$^1$ includes a triazolyl group, and R$^1$ terminates in a pair of ethylglutamate groups, and every R is —OR$^1$. In one example of the porphyrin of Formula (I), the metal is platinum or palladium.

The porphyrin of Formula (I) may be an oxygen-sensitive phosphor whose emission intensity is dependent on oxygen partial pressure. In one example of the porphyrin of Formula (I), the porphyrin can be excited when illuminated at a first wavelength in a range of 350-600 nanometers, followed by emission of phosphorescence at a second wavelength in a range of 600-700 nanometers. The first wavelength can be 532 nanometers, and the second wavelength can be 644 nanometers. The first wavelength can also be 546 nanometers and the second wavelength can be 674 nanometers.

In another embodiment, the compound of the present disclosure is a phosphorescent meso-unsubstituted porphyrin having the Formula (II):

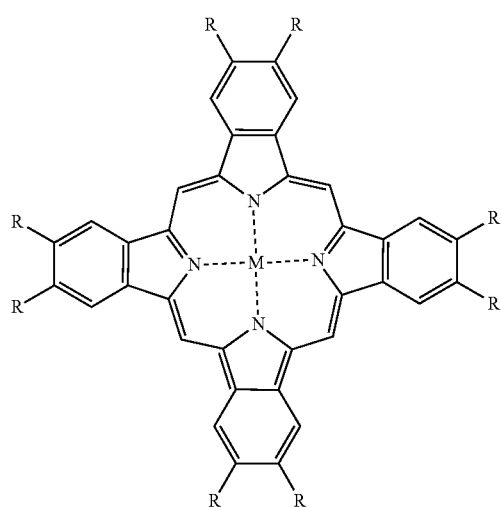

(II)

In the porphyrin of Formula (II), $R^1$ may be selected from the group consisting of hydrogen, substituted or unsubstituted alkyl, substituted or unsubstituted alkyl carbonyl, substituted or unsubstituted alkenyl, substituted or unsubstituted alkynyl, substituted or unsubstituted cycloalkyl, substituted or unsubstituted heterocycloalkyl, substituted or unsubstituted aryl, heteroaryl, halo, cyano, and nitro. In one example of the porphyrin of Formula (II), $R^1$ is hydrogen. In another example of the porphyrin of Formula (II), $R^1$ is alkynyl, such as 2-propynyl (propargyl). In the porphyrin of Formula (I), a plurality of R can be —$OR^1$, and optionally, every R can be —$OR^1$.

In one example of the porphyrin of Formula (II), $R^1$ includes a triazolyl group. The triazolyl group may be bonded to O via an alkyl chain. In one example of the porphyrin of Formula (II), $R^1$ includes an alkylglutamate group. $R^1$ may terminate in a pair of alkylglutamate groups. In another example of the porphyrin of Formula (II), $R^1$ includes a triazolyl group, and $R^1$ terminates in a pair of ethylglutamate groups, and every R is —$OR^1$. In one example of the porphyrin of Formula (II), the metal is platinum or palladium.

The porphyrin of Formula (II) may be an oxygen-sensitive phosphor whose emission intensity is dependent on oxygen partial pressure. In one example of the porphyrin of Formula (II), the porphyrin can be excited when illuminated at a first wavelength in a range of 350-650 nanometers, followed by emission of phosphorescence at a second wavelength in a range of 700-800 nanometers. The first wavelength can be 594 nanometers, and the second wavelength can be 740 nanometers. The first wavelength can be 605 nanometers, and the second wavelength can be 770 nanometers. The first wavelength can also be 600-615 nanometers and the second wavelength can be 760-800 nanometers.

The present disclosure also provides a method for making a porphyrin. The method includes the step of forming a porphyrin ring via a condensation reaction of a compound of formula (III)

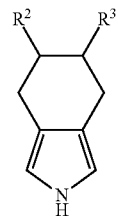

(III)

wherein $R^2$ is an atom or a group of atoms, wherein $R^3$ is an atom or a group of atoms, and wherein at least one of $R^2$ and $R^3$ is —$OR^4$, wherein $R^4$ is an atom or a group of atoms. In the method, $R^4$ may be selected from the group consisting of hydrogen, substituted or unsubstituted alkyl carbonyl, substituted or unsubstituted alkyl, substituted or unsubstituted alkenyl, substituted or unsubstituted alkynyl, substituted or unsubstituted cycloalkyl, substituted or unsubstituted heterocycloalkyl, substituted or unsubstituted aryl, heteroaryl, halo, cyano, and nitro. In one version of the method, $R^2$ is —$OR^4$, and $R^3$ is —$OR^4$. In one version of the method, $R^4$ is alkyl carbonyl, such as a $C_1$-$C_{10}$ alkyl carbonyl, e.g., tert-butyl carbonyl (also known as trimethylacetyl or pivaloyl).

In one version of the method of the present disclosure, the compound of formula (III) is condensed to a tetracyclohexenoporphyrin. The tetracyclohexenoporphyrin may be used to synthesize, via metallation, a phosphorescent meso-unsubstituted porphyrin having the Formula (I) above. The tetracyclohexenoporphyrin may also be used to synthesize, via oxidation and metallation, a phosphorescent meso-unsubstituted porphyrin having the Formula (II) above. In the porphyrin of Formula (I) or the porphyrin of Formula (II) produced by the method of the present disclosure, $R^1$ may be selected from the group consisting of hydrogen, substituted or unsubstituted alkyl, substituted or unsubstituted alkyl carbonyl, substituted or unsubstituted alkenyl, substituted or unsubstituted alkynyl, substituted or unsubstituted cycloalkyl, substituted or unsubstituted heterocycloalkyl, substituted or unsubstituted aryl, heteroaryl, halo, cyano, and nitro. $R^1$ can be hydrogen, or $R^1$ can be alkynyl, such as 2-propynyl (propargyl). In the porphyrin of Formula (I) or the porphyrin of Formula (II) produced by the method of the present disclosure, a plurality of R can be —$OR^1$, and optionally, every R can be —$OR^1$. $R^1$ can include a triazolyl group. The triazolyl group may be bonded to O via an alkyl chain. In the porphyrin of Formula (I) or the porphyrin of Formula (II) produced by the method of the present disclosure, $R^1$ may include an alkylglutamate group. $R^1$ may terminate in a pair of alkylglutamate groups. $R^1$ may include a triazolyl group, and $R^1$ may terminate in a pair of ethylglutamate groups, wherein every R is —$OR^1$. In the porphyrin of Formula (I) or the porphyrin of Formula (II) produced by the method of the present disclosure, the metal may be platinum or palladium.

The present disclosure also provides a method for measuring oxygenation in tissue of a subject (e.g., an animal, preferably a mammal, most preferably a human). The method includes the steps of positioning a compound of Formula (I) or Formula (II) adjacent to the tissue of the subject, causing the compound to phosphoresce, and calculating an oxygen pressure based on phosphorescence intensity and/or phosphorescence lifetime of the compound. The compound may be associated with a matrix incorporated in a dressing that is placed on a tissue surface (e.g., skin).

One non-limiting example of the present disclosure is a group of four meso-unsubstituted, metallated porphyrins that can be the core component around which macromolecular structures can be built that will function as oxygen sensing materials for a number of biomedical applications including, but not limited to, cellular level cancer-related hypoxia imaging and non-invasive oxygenation or perfusion assessment in skin burns, acute and chronic wounds.

The planar structure of these porphyrins of the present disclosure, which is enabled by the lack of substituents in the meso positions of their central ring, imparts upon them large absorption cross-sections and unusually bright emissive properties, thereby classifying them among the most brightly phosphorescent porphyrin molecules. The different spectral features these molecules exhibit, comprising multiple different excitation bands spanning over most of the visible region of the spectrum and different emission profiles, enables them to function as a set of versatile imaging tools compatible with the most widely used imaging equipment. The compounds also exhibit phosphorescence lifetimes of 40 microseconds to 1 millisecond. Photophysical studies show that they exhibit both higher absorption coefficients and phosphorescence quantum yield relative to most known porphyrins. As a result, it is anticipated that these molecules will be highly beneficial in numerous oxygen measurement applications, as they can be excited with a variety of readily available laser sources, and they output much brighter signal which makes signal collection and analysis more efficient.

Synthetically, these molecules can be functionalized with alkyne peripheral groups, making them compatible with a highly efficient and rapid synthetic modification methodology known as 1,3-Huisgen cycloaddition (usually termed as "click chemistry"). This elegant synthetic approach is widely used by researchers who are developing macromolecular structures for use in biomedical applications, including those performing research in the oxygen-imaging field. Notably, the use of the straightforward "click" methodology enables non-specialists to modify and functionalize the porphyrins using straightforward synthetic procedures.

This invention offers the research community a variety of oxygen-sensing cores that can be readily and efficiently functionalized within higher order structures; importantly, these structures will be compatible with currently available imaging technology for use in a wide variety of oxygen sensing applications. Due to the synthetic protocols that exist for growing molecules using "click chemistry" along with the fact that there is a large number of researchers having experience with that methodology, it is anticipated that the porphyrin molecules described herein will be extremely useful as essential components for building macromolecular structures for oxygen imaging applications. Additionally, chemically protected synthetic intermediates can become available as oxygen-sensing cores for researchers who wish to further explore synthetic alternatives that require the introduction of different peripheral functional groups.

In the compound of the present disclosure, the existence of all alkyne-terminal groups on the periphery in one version of the compound, allows their functionalization via the rapid and synthetically highly efficient 1,3-Huisgen cycloaddition reaction (usually referred to as "click chemistry"), a methodology in covalent assembly of large molecules.

The enhanced brightness of the new porphyrins together with the ability to be readily excitable with common laser lines found in commercial microscopes, is a combination of characteristics not being found in products that are currently commercially available.

The optimized synthetic protocol developed for the synthesis of the new molecules, which is at least partly the result of the use of a stable protecting group during the steps required to modify synthetic intermediates, will allow the production of the final porphyrins in large quantities and with high yield.

These and other features, aspects, and advantages of the present invention will become better understood upon consideration of the following detailed description, drawings, and appended claims.

BRIEF DESCRIPTION OF THE DRAWINGS

Like reference numerals will be used to refer to like parts from Figure to Figure in the following description of the drawings.

DETAILED DESCRIPTION OF THE INVENTION

Certain implementations of the present invention may include a dressing. Herein, a dressing may include a covering for application to a surface and especially for application to a surface of a body part of a patient. The term dressing may also apply to other coverings, such as an ointment or gauze and may be a solid of liquid. The terms dressing, bandage, covering and related terms may be used throughout the disclosure to refer to a covering.

Figure 1:
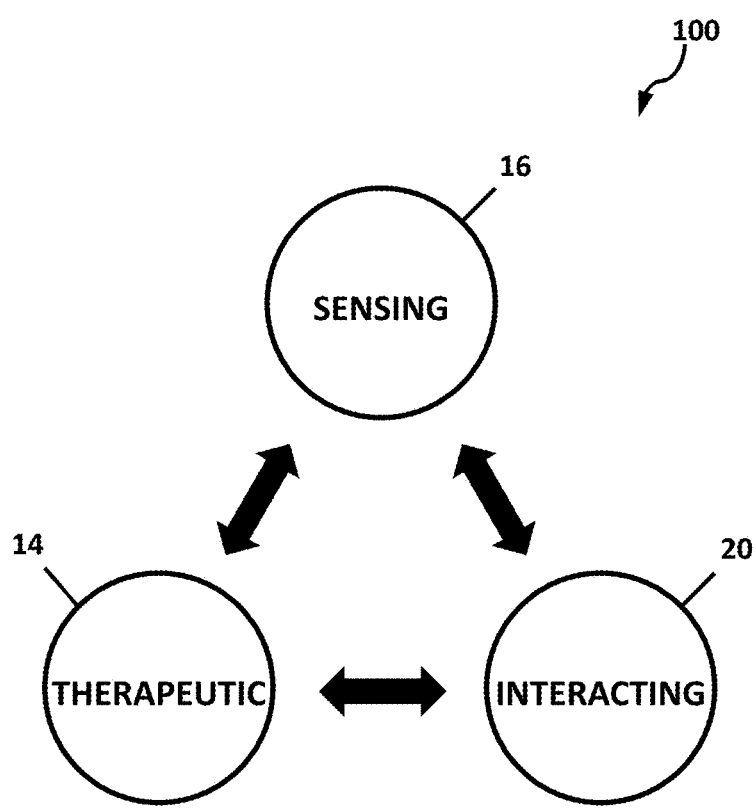
FIG. 1 is a schematic illustration of exemplary components of a dressing in accordance with the present invention.
Figure 2A:
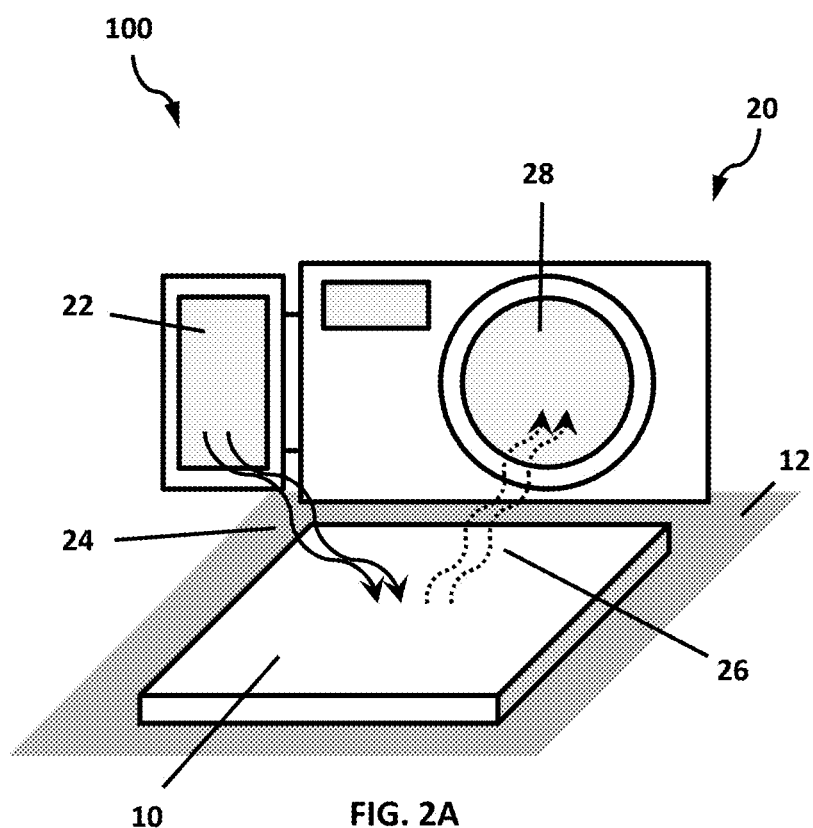
FIG. 2A is a schematic illustration an embodiment of the present invention including a sensing/therapeutic device and an interacting device.

In one embodiment, the present invention is a bandage/wound dressing device 100 having one or more of the following three components: a sensing portion 16, a therapeutic portion 14, and an interacting portion 20, as illustrated in FIG. 1. The device 100 is contactable and, preferably, removably adhereable to body surface, such as intact and/or open/damaged tissue. The present device 100 may be used by a "user", wherein the user may be, for example, a patient's caregiver, a physician, or even a patient. In one embodiment, the present invention may be a device 100 including a sensing/diagnostic portion 16. The diagnostic portion 16 can be combined with an interacting portion 20 (for example, a detector) to measure a signal from the diagnostic portion and provide an output to a user. In another embodiment, the present invention may be a device 100 including both a sensing portion 16 and a therapeutic portion 14. Referring to FIG. 2A, in yet another embodiment, the device 100 may include two distinct but interdependent devices: a dressing 10 including both diagnostic and therapeutic portions as described above and an interacting portion 20.

Figure 2B:
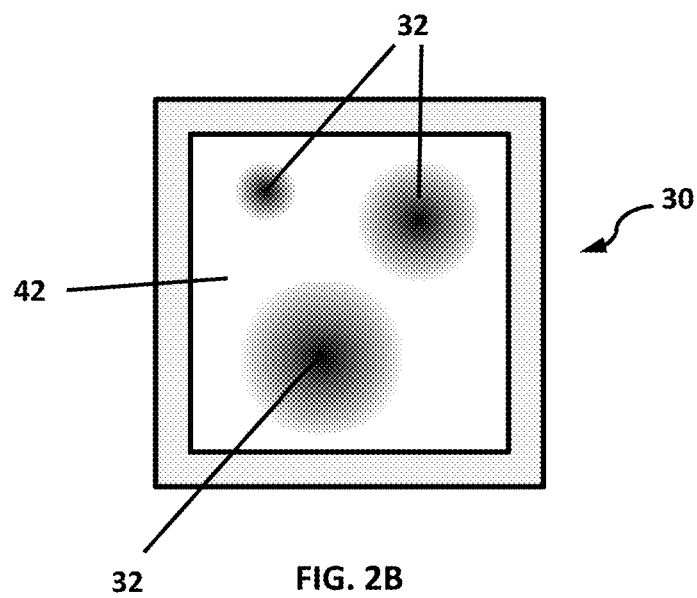
FIG. 2B is a schematic illustration of an example of 2-dimensional data acquired with a device of the present invention.

Generally, the present invention is capable of performing several functions. Referring to FIG. 2B, the present invention is capable of generating a two-dimensional map 30 of physiologically relevant parameters, where each point on the map corresponds to a scalar value corresponding to data relevant to one or multiple analytes in the underlying tissue, such as the concentration of the analyte or analytes. In one aspect, the map can be read either continuously or point-wise by the naked eye as a colorimetric sensor response, the quantitative signal can be stimulated and recorded using the interactive device, or the quantitative signal can be collected by an external digital recording device. In the embodiment illustrated in FIG. 2B, the dark points 32 on the map are distinct from the white points 42 indicating a variation in the spatiospecific signal detected. Further, the present invention is capable of administering doses of therapeutics, such as, but not limited to, antibiotics, anti-inflammatory agents, biologics, and pain medications. Also, the present invention is capable of administering a dose of biomarkers or positron emission tomography tracers along with or instead of the therapeutics. Even further, the present device is capable of administering these therapeutics in a controlled manner in response to a specific externally applied stimulus or stimuli. This release can be accomplished through stand-alone mechanisms independent of interacting portion, such as, but not limited to, mechanical pressure, heat, other energetic stimulus or through a stimulus generated by the interactive device such as, but not limited to, light or ultrasound. Further, the present device is capable of monitoring the quantity of therapeutics and/or the delivery location on the device's surface which can be recorded and/or tracked using either a colorimetric change that occurs during or after the delivery process or monitored using the interacting portion. The present device also is capable of storage, processing, visualization, and/or transmission of data.

Measurements of parameters, such as tissue parameters, are made using sensor elements that are capable of providing feedback to the user directly or indirectly. These sensor elements may not be in direct contact with the tissue. In one aspect, the sensor elements are contained and/or compartmentalized within the sensing portion, which is in physical contact with the underlying tissue. Readout and quantification of tissue parameters can be made through optical means for signal detection from species including, but not limited to, chromophores, fluorophores, or phosphors whose absorption or emission properties change based on their passive or active interaction with the tissue. The signal may be responsive to the analytes by modulation of inelastic scattering of an electromagnetic field, including such mechanisms as phosphorescence, fluorescence, absorption, and the like.

It is possible to alter and set the excited state lifetimes of a sensor. Excited states of a molecule have intrinsic lifetimes during which they can be populated. These lifetimes are dependent on an array of parameters, including molecular structure, temperature, solvation condition, surrounding molecules, and chemical interactions to name a few. The lifetime of these states can be important in the development of optimal sensors, especially in the case of oxygen sensing. For example, tissues in the body contain natural molecules that are fluorescent, such that exposure of tissue to certain wavelengths of light can lead to fluorescent emissions. The signal strength of these emissions can be larger or comparable to the emissions of some sensing molecules. To separate the emission of the sensor from fluorescence, it is possible to chemically create a sensor whose emissive excited state lifetime is longer than the states of molecules in tissue who give rise to fluorescence emission. If one creates a molecule whose excited state is a so-called triplet state, and this triplet state leads to phosphorescence, then it is possible to temporally distinguish a molecule's phosphorescence from fluorescence. For example, the oxygen sensor Oxyphor R2 has a maximum phosphorescence lifetime of almost 1 millisecond, a lifetime that is one thousand times longer than the longest tissue fluorescence source. By using a short temporal illumination (e.g. 1 microsecond long) with a camera system temporally gated to detect signals emitted at longer lifetimes (e.g. 500 microseconds after the illumination burst) it is possible to selectively detect only the phosphorescence without detecting the fluorescence signal Any one or more of these sensing portions may be embedded or enmeshed within a compatible matrix that serves to modulate the sensitivity of the sensing portions and/or to enhance the stability and useful lifetime of the sensing portions. This sensor element/matrix combination will hereafter be referred to as the "sensing portion", with the understanding that such terminology encompasses a variety of sensor element/matrix formulations. In certain embodiments, the sensor elements include a foam, hydrogel, polymer or mixture of multiple ingredients of uniform or variable porosity and/or heterogeneous/asymmetric or homogeneous/symmetric dendrimeric structures or layers surrounding each individual sensing element. In some embodiments, the sensor elements include the elements illustrated in FIGS. 2C-E. For example, FIG. 2E lists elements included in a formulation for a liquid bandage. The active ingredients include benzethonium chloride and the inactive ingredients include amyl acetate, benzalkonium chloride, castor oil, oil of cloves (eugenol, carophyllene), ethanol, n-butyl acetate and nitrocellulose.

Note that optical readout is only one of a variety of informational displays in accordance with the present invention and the invention therefore is not necessarily limited to an optical quantification interface. In one specific embodiment, a feature of the present invention is the containment of these sensing/reporting agents in a compartment or series of compartments separated from the tissue by a semipermeable layer to prevent direct interaction of the tissue and/or biological fluids with the sensor elements, as well as with unreleased therapeutics. Integral aspects of the semipermeable membrane include its ability to physically separate the sensing elements and therapeutics from the tissue, and selectively allow the physiological analyte or analytes of interest to pass through and interact with the sensor elements and/or the therapeutic-encapsulating matrix. The analyte or analytes may be any number of biologically relevant species, including but not limited to molecular oxygen, carbon dioxide, nitric oxide, dissolved analytes in plasma, and hydrogen ions. The invention's interactive features can be implemented through a single "sandwich" type construction, in which the invention's spatial resolution is determined by the natural diffusion radius of the analyte throughout the matrix, or through the formation of multiple compartments physically arrayed across the invention.

If the analyte or analytes of interest are skin-impermeable or are otherwise unable to reach the sensor apparatus (such as gases in capillary beds below the epidermis), one embodiment of the invention cab makes use of penetrative features that reside on or are arrayed across the bottommost surface of the invention, in contact with the user's tissue, such as needles or microneedles. These penetrative features, will either permeabilize or penetrate whatever occluding layers (for example, skin, burn eschar) that fall between the bottom layer of the invention and the analyte(s) of interest, thereby facilitating more accurate and more rapid measurements. Another approach is to utilize fractionated laser therapy technology to create micrometer sized holes in the tissue that can enable the diffusion of analytes across the tissue surface. Such an approach can be deployed prior to the placement of the invention or during its use to facilitate to movement of analytes across normally impermeable tissues. Note that these are only two embodiments of this feature (that is, a methodology for bringing the analytes across a diffusion barrier and into contact with the sensor apparatus); many other embodiments and variations may also be used.

Regarding therapeutic encapsulation, in certain embodiments, the present invention is capable of delivering one or more therapeutic agents to surface in contact with the invention. For example, a user can determine to release a therapeutic from the invention due to perceived need or based on feedback provided by the invention. Therapeutics can be embedded in a degradable matrix that is affixed to, or is part of the invention. Embedding of therapeutics can be accomplished through a number of means, such as physical encapsulation (for example, in poly(lactic-co-glycolic) acid (PLGA), polydimethylsiloxane (PDMS), or another polymer matrix) or covalent bonding via a reactive chemical linker that releases therapeutics in response to a physical, chemical, or other stimulus (for example, light, pressure, or thermal changes). The therapeutics can also be embedded in particles, such as nanoparticles. The matrix in which the therapeutic is embedded, hereafter referred to as the "therapeutic apparatus," can include, but is not limited to, polymers, such as PLGA or polystyrene, a mixture of multiple polymers, or other material classes, such as dendrimers, hydrocolloids, or hydrogels. The therapeutic apparatus may be applied to either specific regions of the invention or the entire invention to facilitate therapeutic release at user-determined spatial locations on the inventive device. The invention can also include multiple compartments, each of which contains a different therapeutic or therapeutic mixture, all of which can be released by the user at selected spatial locations in a dose-controlled manner through application of the aforementioned external stimulus. As such, the invention can act to both store and deliver multiple therapeutics, thereby providing, in one embodiment, a novel multi-therapeutic delivery platform.

Figure 3A:
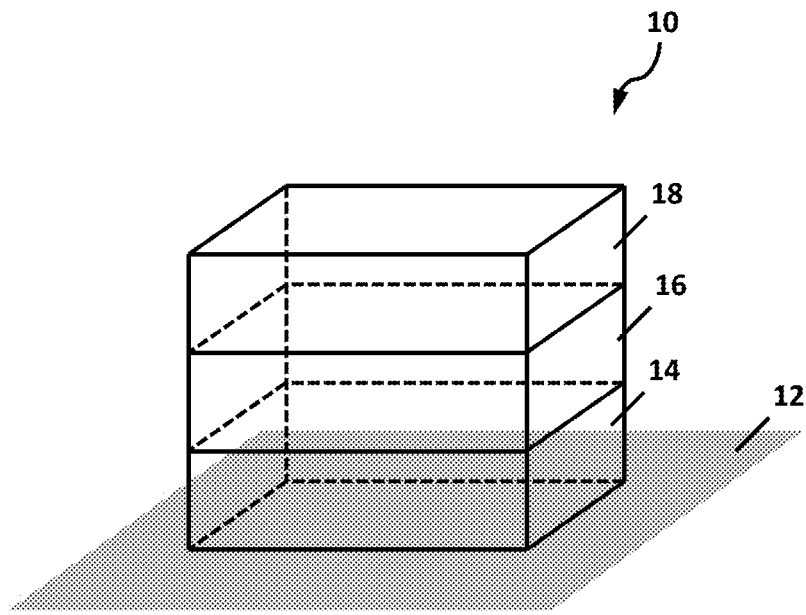
FIG. 3A is perspective illustration showing an example of a stacked structure in accordance with the present invention
Figure 3B:
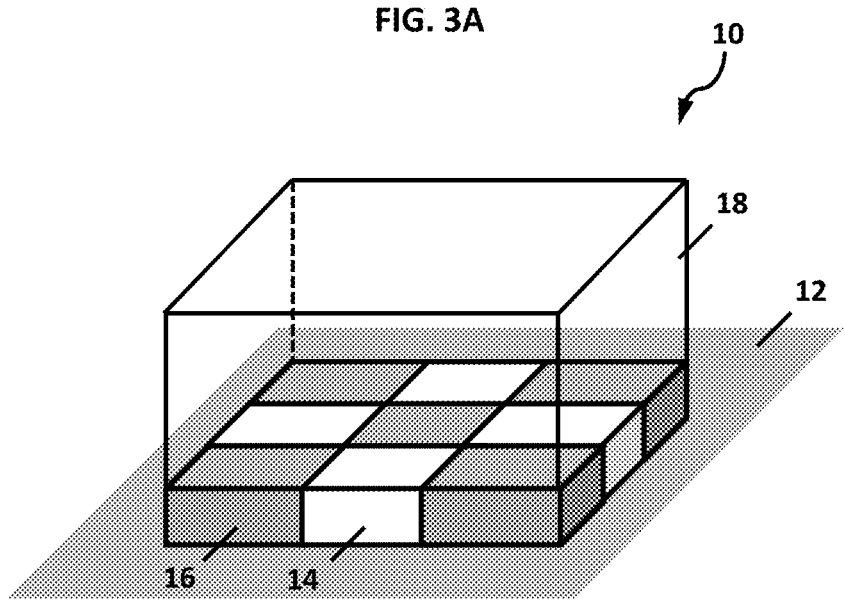
FIG. 3B is a perspective illustration showing an example of an interleaved structure in accordance with the present invention.
Figure 4:
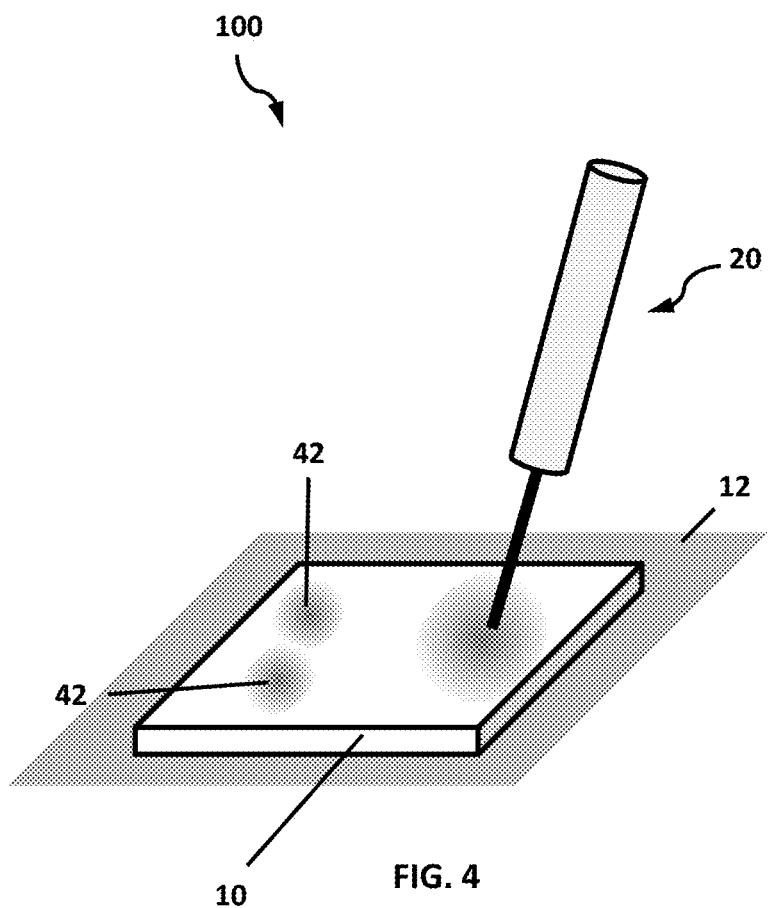
FIG. 4 is a schematic illustration of an alternate embodiment of a device of the present invention.

Referring to FIGS. 3A-B, the invention can be constructed in different geometrical formats to optimize both sensing and therapeutic delivery functionality, such as, but not limited to, (i) a vertically stacked structure as illustrated in FIG. 3A, in which the therapeutic apparatus 14 resides physically below the sensing apparatus 16; (ii) an interleaved structure as in FIG. 3B, where the sensing 16 and therapeutic 14 apparatus are patterned in the same layer; (iii) a mixed structure in which the sensing apparatus and therapeutic apparatus are physically combined; and (iv) combinations thereof or variations therefrom. The mixed structure allows for the therapeutic apparatus to share common components with the sensor apparatus, as well as for the two matrices overlapping and/or otherwise coinciding within the same structure. In addition, the device 10 can have a top layer 18, which can function as a barrier layer or an enhancing layer. In both FIGS. 3A and 3B, the device 10 is applied to a surface 12, which can be a surface of a body part such as skin tissue.

If the therapeutic delivery target is not physically adjacent to the immediate tissue layer(s) in contact with the invention (such as capillary beds below the epidermis), one embodiment of the invention makes use of penetrative features, such as needles, that reside on or are arrayed across the bottommost surface of the invention, and are in contact with the user's tissue. These features, which may be microscopic, will permeate or penetrate whatever occluding layers reside between the bottom layer of the invention and the therapeutic target. Fractional laser therapy can additionally be used to create micrometer-sized holes in the tissue that can facilitate the motion of therapeutics across normally therapeutic-impermeable tissues. Additionally, a chemical agent or combinations of multiple chemical agents that act to improve tissue permeability, either directly or in response to physical stimuli (for example, light, pressure, electrical signals, or thermal changes) can be built in to the invention to facilitate the penetration of therapeutics.

Additionally, the invention can be manufactured to be degradable over time. Many dressings, sutures, and bandages can be configured or manufactured such that the degraded components are not toxic, are not harmful, and/or are safely absorbable by the body. Such dressings can be safely incorporated into a number of devices, implantable probes, or within closed wounds for long-term safe monitoring and/or therapeutic release Regarding therapeutic release, an integral aspect of the therapeutic apparatus is its ability to release therapeutics in response to some external stimulus, including but not limited to light, pressure, mechanical force, or thermal changes. As opposed to existing therapeutic delivery systems, the present invention provides the ability of a user to interactively and spatially control the exact location of therapeutic release into tissue from the invention. Whereas existing devices release therapeutics across a bandage, dressing or patch, the release properties and kinetics of the therapeutic apparatus in this invention can be quantitatively controlled through careful modulation of the applied external stimulus at multiple arbitrary points on the bandage as selected by the user, such that modulation of intensity or duration of the external stimulus will result in delivery of a predetermined dose of therapeutics. A therapeutic apparatus in accordance with the present invention may include a polymer containing or composed of photoactive/photosensitive molecules that trigger or otherwise facilitate therapeutic release in response to applied light at a given bandage position. In this embodiment, the release of different therapeutics may be triggered or potentiated for using different wavelengths of light, thereby creating a simple platform for simultaneous or sequential administration of multiple different therapeutics within the same apparatus. Such a wavelength-triggered therapeutic release could be activated by a user to deliver different therapeutics to different spatial locations across the apparatus.

Light-based release may be restricted to unique devices such as the invention's integrative apparatus, so that only use of a specific source of light will result in therapeutic release. In this way, the release of controlled substances can be monitored and restricted. Such mechanisms can include optical and/or mechanical approaches. For example, therapeutic release can be initiated only by a predetermined pulse of light that conforms to specific parameters that may include, for example predetermined intensity, duration, polarization, wavelength, and wavelength shifts thereof.

In one embodiment, other interactions, such as continuous illumination, may have no effect on therapeutic release. Therapeutics can also be released through mechanical stimulation (such as pressure applied at spatial locations by a user); this pressure can be directly applied to the invention or induced via other means (that is, pressure waves created by light, light pulses, electrical signals, or ultrasound). Such mechanisms can also be used to permeabilize the underlying tissue for facilitated penetration through intact tissue.

Therapeutic release kinetics and spatial administration patterns can also be mediated through the construction of the invention itself. In one embodiment, the bandage can be constructed to have a single therapeutic matrix in which the therapeutics are embedded. In another embodiment, the invention may be composed of discrete regions, each of which contains a different therapeutic, therapeutic dose, or a combination of the two. In yet another embodiment, each discrete region has different therapeutic release kinetics that may be determined by the chemical properties of the selected therapeutic matrix. In all the previously described implementations, each discrete region can be constructed to release a therapeutic singly or in combination with other therapeutics in response to a variety of user-provided exogenous signals, such as different wavelengths of light applied to spatial locations on the invention. In this manner, the invention can suit a wide variety of applications. For example, therapeutic release can be achieved with light of different color throughout the visible spectrum. Examples are blue light (450-495 nanometers), green light (495-570 nanometers) or orange light (590-620 nanometers).

With respect to the monitoring aspect of the present invention, the same mechanisms that provide for the reporting of tissue parameters can additionally be used post-treatment to monitor therapeutic response. If the clinical response is not perceived to be adequate, additional amounts of therapeutic can be released from the invention via the user-controlled release mechanisms discussed above.

Another aspect of the present invention relates to data storage, processing, visualization, and transmission. The delivery agent or control scheme used to facilitate or trigger therapeutic release can be part of an interactive, programmable system for controlled, metered therapeutic release and reporting. An interacting apparatus configured to effect pressure, sonic, light, electric, or other energy-based therapeutic release can be programmed to release a given amount of therapeutic in a given time interval at a selected spatial location, and can be reprogrammed or updated "on the fly" by a caregiver, physician, or remote administrator. The therapeutic delivery system can be interactively programmed securely over a network, intranet, or over the internet through wired or wireless communication, or a networked docking station, all providing a link to a local computer or remote server/computer. This remote link can be used in monitoring the dose and frequency of therapeutic administration and to inform a physician or caregiver, and be remotely programmed to allow for changes in therapeutic dose or type. Moreover, the delivery scheme can incorporate sensors that readout regions of the invention to inform a caregiver or clinician of relevant tissue parameters and tissue response. Tissue parameters, treatment response, and all acquired data can be stored, processed, and visualized, either locally or remotely. Data storage, processing, and visualization can be accomplished using the interacting apparatus itself, a docking station, or a computer or mobile device. Thus, the invention also provides a "point-of-care" technology that enables more effective utilization of in- and out-patient clinical resources. Such a technological approach may be compatible with efforts in point-of-care medicine, such as monitored home use and kiosk-based patient interactions.

Figure 2C:
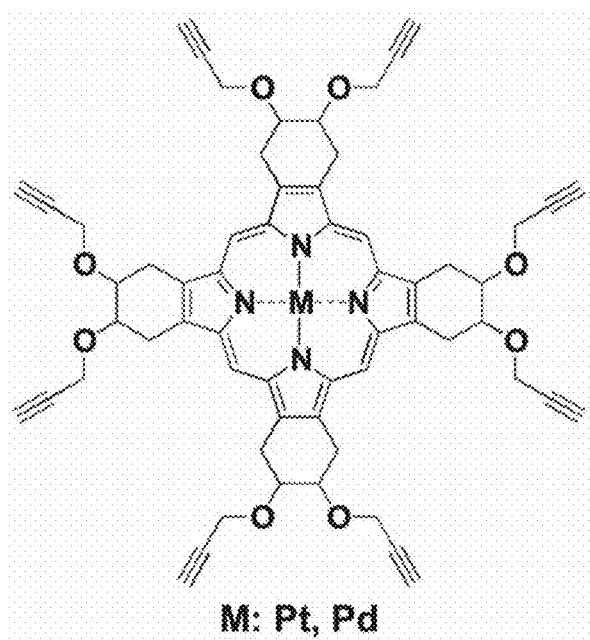
FIG. 2C is a diagram of an exemplary structure of metallated porphyrin that may be employed with the present invention.
Figure 6A:
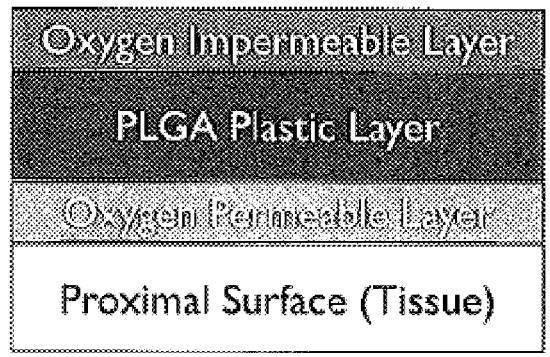
FIG. 6A is a schematic illustration of one sensing portion in accordance with the present invention.

FIGS. 2A-B illustrate one embodiment of the device 100 in which a dressing 10 has a sensing matrix layer that includes an oxygen-sensitive phosphor whose emission intensity is dependent on oxygen partial pressure. An interacting device 20 includes an actuating portion 22 and a detecting portion 28. The actuating portion generates an actuating signal 24 and the detecting portion 28 detects a response signal 26. In the illustrated embodiment, the oxygen sensitive phosphor within the dressing 10 can be actuated 24 and a corresponding measure of phosphorescence 26 can be translated into oxygen concentrations. The sensing matrix further includes an oxygen-permeable polymeric matrix that has the phosphor embedded into it and serves as a solid support for the sensor element. In one embodiment of this invention, the sensor element may be a construct in which a metallated porphyrin, such as illustrated in FIG. 2C, is physically or covalently encapsulated inside a dendritic layer. The dendritic layer serves to attenuate oxygen diffusion towards the core, thus protecting the porphyrin from excessive quenching and increasing its sensitivity to small changes in oxygen pressures. Excitation and subsequent emission of the phosphor can be used to determine oxygen tension. Specifically, tissue oxygen tension, which is the partial pressure of oxygen (usually reported in mmHg or Torr) within the vapor that is in equilibrium with the tissue of interest, can be determined. For example, tissue oxygen tension is proportional to the average oxygen concentration inside the cellular and extracellular components of the tissue and, accordingly, can be determined. In another embodiment of the invention, the oxygen sensor can be excited using indirect excitation via energy transfer from a second fluorophore. The sensor is embedded into a polymeric matrix that allows oxygen to freely diffuse through it, and is solely used as a solid support for the sensing element. The sensing apparatus is combined with the therapeutic release apparatus, and is separated from the therapeutic release apparatus via an oxygen-permeable membrane. In certain embodiments, the sensing apparatus is isolated from ambient oxygen pressure via an oxygen-impermeable membrane that comprises the top layer of the bandage apparatus as illustrated in FIG. 6A.

Figure 2D:
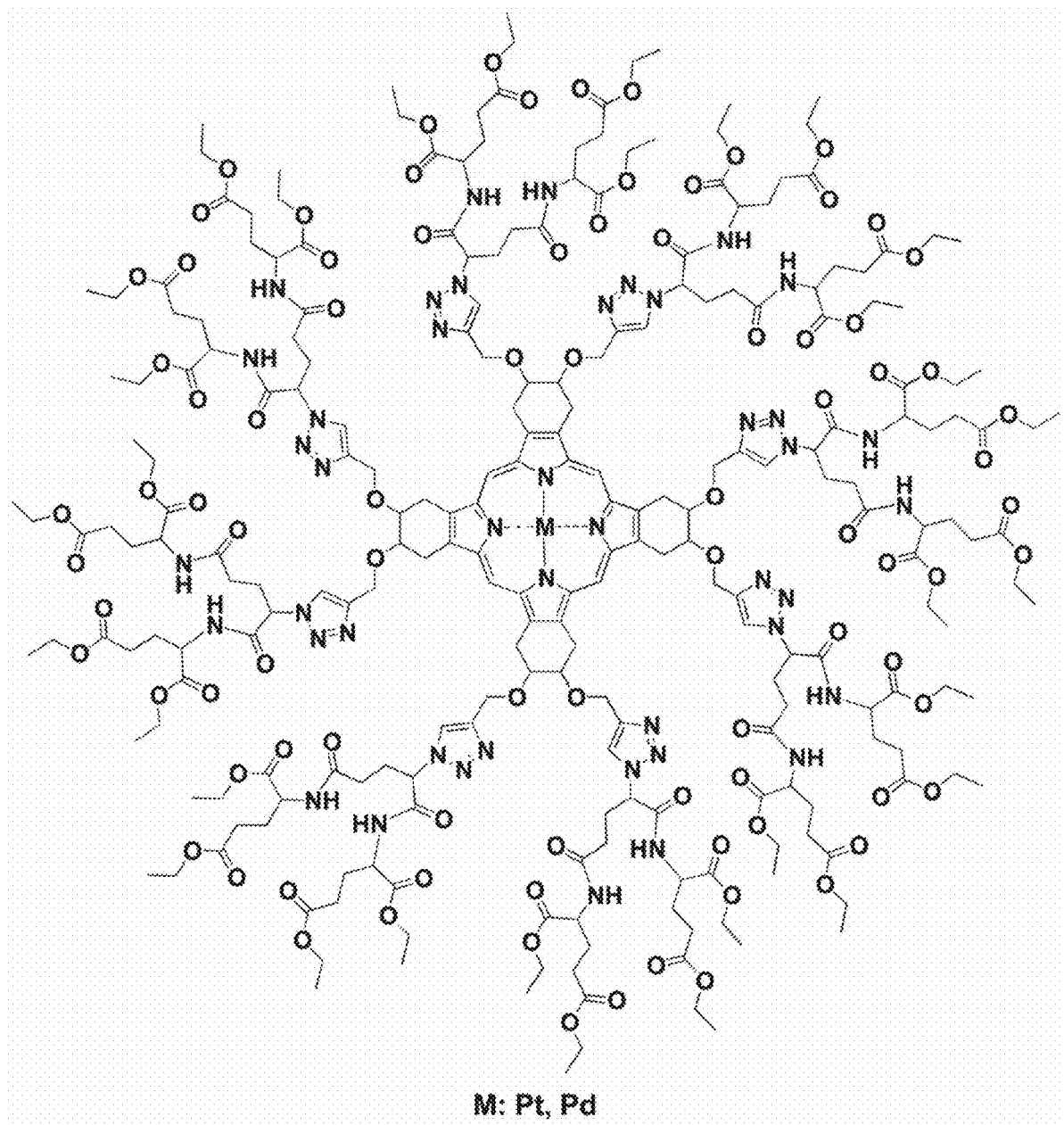
FIG. 2D is a diagram of an exemplary structure metallated porphyrin-dendrimer that may be employed with the present invention.
Figure 2E:
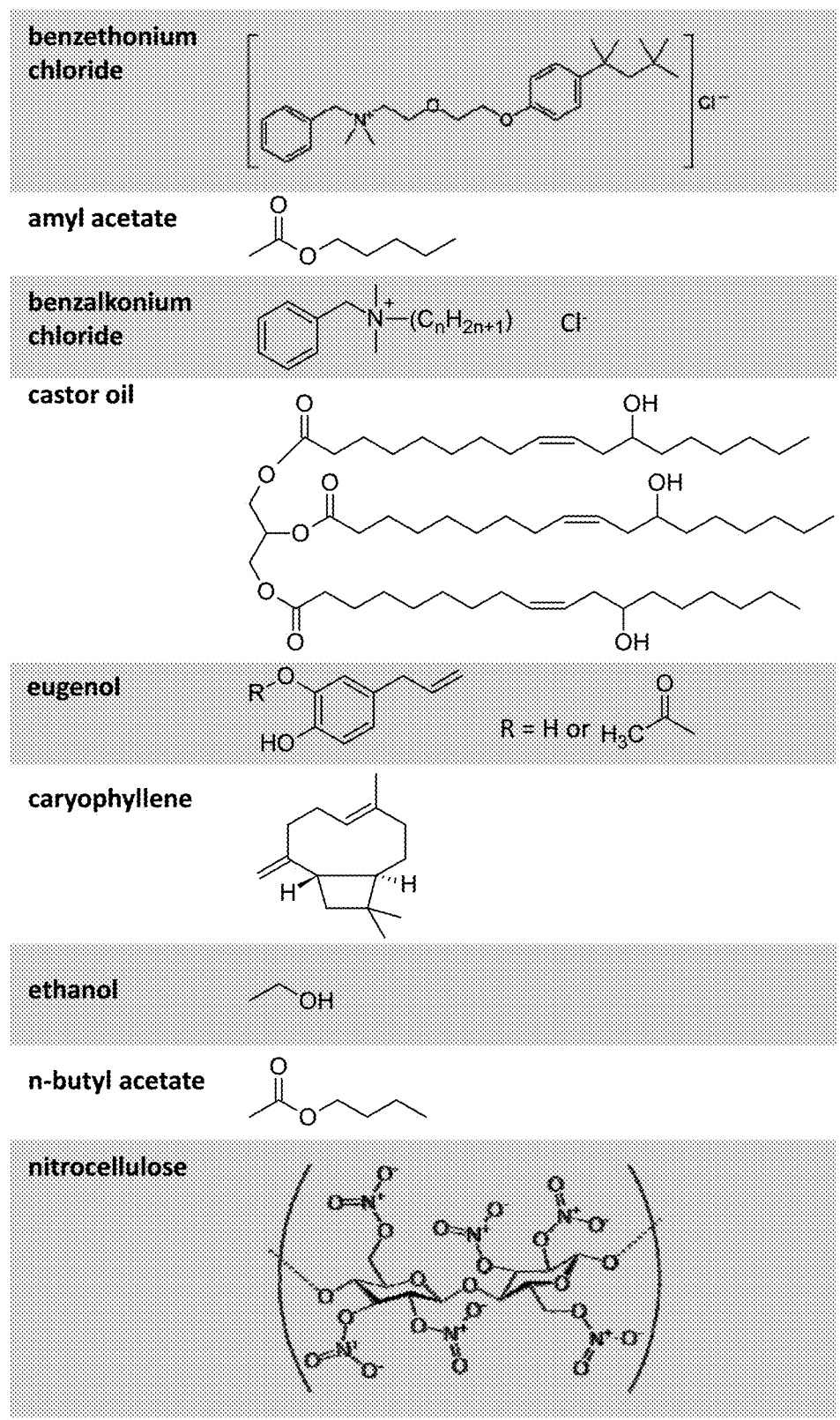
FIG. 2E lists elements included in a formulation for a liquid bandage.
Figure 5:
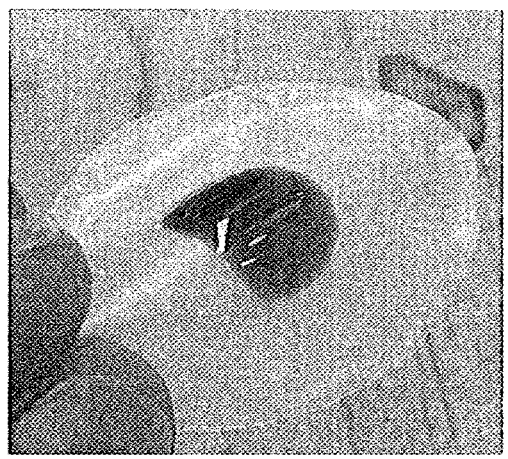
FIG. 5 shows an example of a polymer sensing portion including a meso-unsubstituted platinum porphyrin embedded in a layer of PLGA dried on the surface of a wax film. The polymer sensing matrix is flexible and readily adheres to the hydrophobic wax film.

As a specific example, a brightly emissive, custom built meso-unsubstituted platinum-porphyrin is encapsulated inside a second generation glutamic dendrimer, such as illustrated in FIG. 2D. Glutamic dendrimers are known in the art, and have been successfully employed in increasing the sensitivity of various metallated porphyrins towards oxygen. Referring to FIG. 5, the sensor is embedded into a layer of poly(lactic-co-glycolic acid) (PLGA) adhered to an oxygen-permeable plastic material that separates it from the release therapeutic apparatus. In this example the porphyrin-dendrimer sensor element can be excited when illuminated at 532 nanometers, followed by emission of phosphorescence at 644 nanometers whose intensity can be used as an indicator for oxygen concentration. Of course, other excitation and emission examples are likewise contemplated. For example, other excitation/emission examples for different sensors, include (i) excitation at 546 nanometers and emission at 674 nanometers; and (ii) excitation at 594 nanometers and emission at 740 nanometers.

Figure 6B:
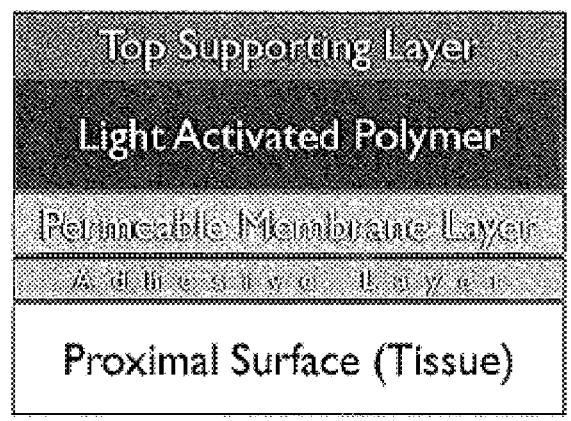
FIG. 6B is a schematic illustration of one therapeutic portion in accordance with the present invention.
Figure 7:
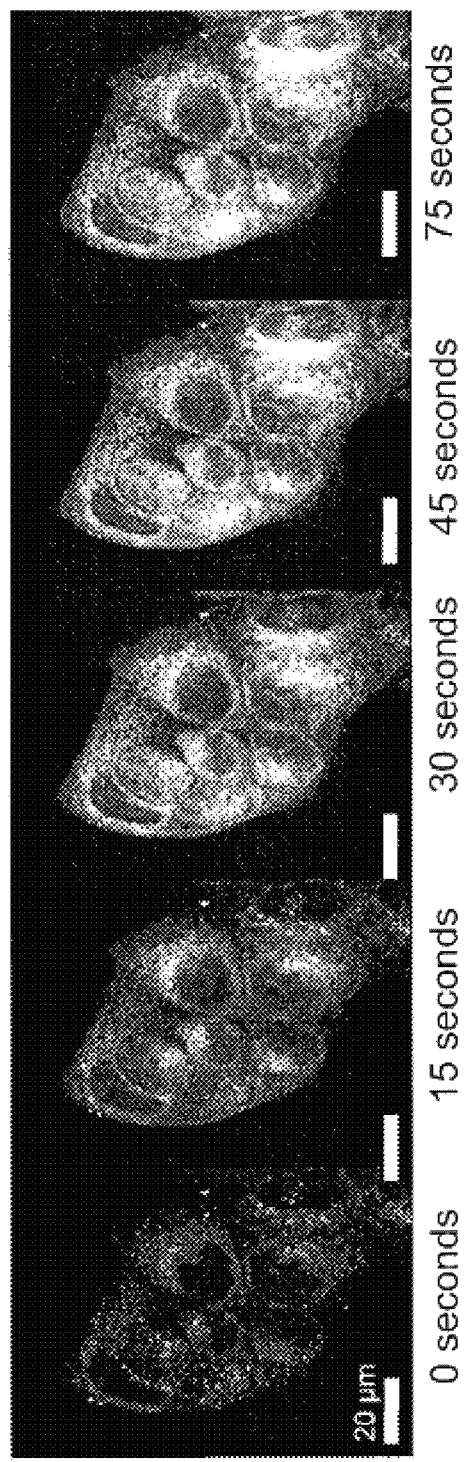
FIG. 7 provides a series of exemplary images showing photobrightening upon 660 nanometer illumination demonstrating light-mediated therapeutic release from PLGA nanoparticles in a biological system.

In one embodiment of this invention, a therapeutic agent is embedded in a light actuated polymer patterned on the proximal surface (that is, the surface closest to the body surface) of a patch (a supporting layer). In one embodiment, the light actuated polymer contains a photoactive molecule embedded in the polymer. In another embodiment, the light actuated polymer contains a light-actuated moiety within the polymer chemical structure. Referring to FIG. 6B, this polymer layer can either be directly adhered to the proximal surface using an adhesive layer, or can be separated from the adhesive by a permeable membrane layer. When irradiated by light, the photoactive compound leads to structural degradation of the polymer, facilitating local therapeutic release. It is known in the art that therapeutics can be readily released from polymer encapsulation using select wavelengths of light. Photosensitizer molecules used in photodynamic therapy can be encapsulated in PLGA polymer nanoparticles for enhanced uptake and delivery to cells and biological tissues. In a previous study, the photosensitizer (and fluorophore) 5-ethylamino-9-diethylaminobenzophenothiazinium (EtNBS) was encapsulated in 120 nanometer diameter PLGA polymer nanoparticles and delivered to both cells and model ovarian cancer tumors. When encapsulated, the close proximity of the photosensitizers acts to quench absorption and emission properties of the particles, such that when encapsulated, illuminated EtNBS-PLGA particles weakly emit fluorescence. When intense red light is delivered to the nanoparticles, the radical species generated by EtNBS act to physically degrade the PLGA polymer structure, leading to the release of the therapeutic from the nanoparticle. Referring to FIG. 7, the effect is observed as photo-brightening in samples containing the nanoparticles, as release of EtNBS negates quenching and results in increased fluorescence emission intensity.

Figure 8:
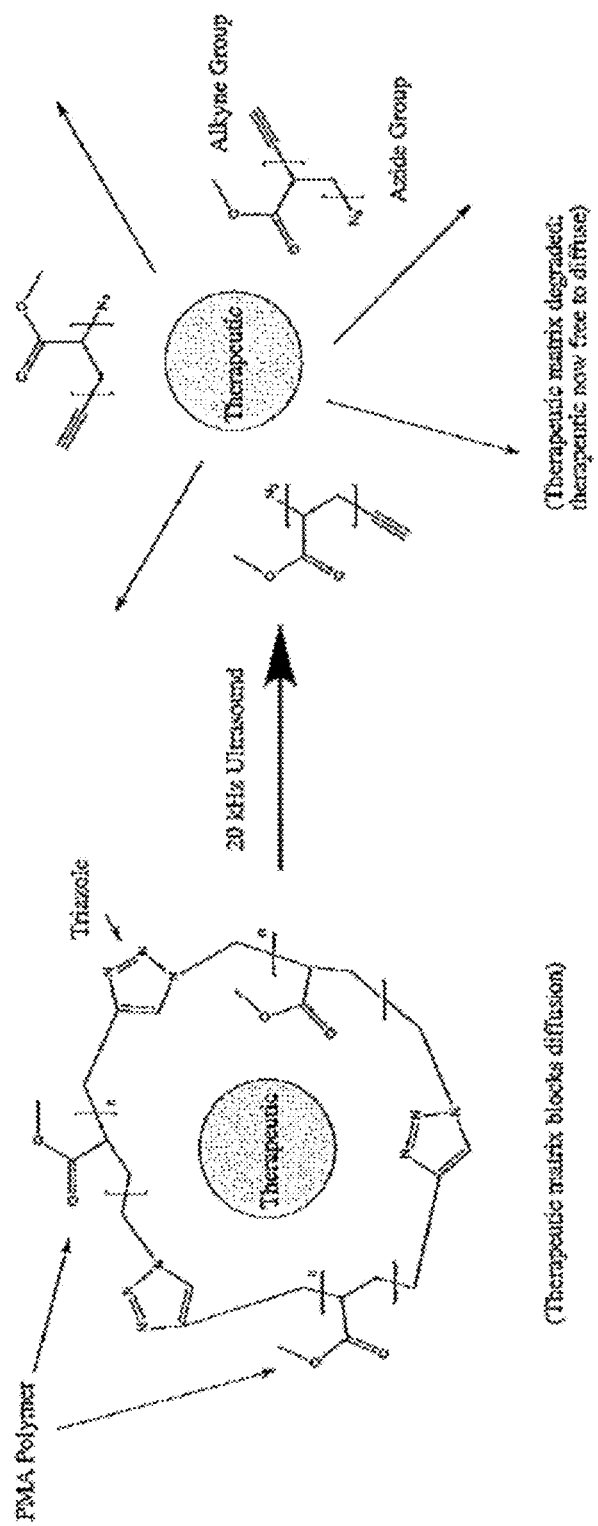
FIG. 8 illustrates one embodiment of the invention therapeutic delivery application using ultrasonic cleavage of triazole-bridged polymer to facilitate therapeutic diffusion and release

Another embodiment of a therapeutic release mechanism may involve the cleavage of chemical bonds within the therapeutic apparatus via ultrasound, leading to controlled therapeutic release due to enhanced or facilitated diffusion through the degraded therapeutic matrix material. In this embodiment, the therapeutic is enmeshed in or chemically bonded to the therapeutic matrix material via chemical moieties known as triazole linkers. Each triazole linker is attached to a long (~100 kDa) polymer linker such as polymethacrylate (PMA), resulting in the formation of a polymer/triazole network, the porosity of which can be tuned chemically. As demonstrated by Bielawski et al., application of 20 kHz ultrasonic pulses to triazole/PMA in solution can result in localized superheating and the formation of vapor-filled vacuoles, the rapid collapse of which resulted in application of attendant stress to the long polymer chains and subsequent mechanical scission of the triazole linkers, resulting in the formation of PMA azides and alkynes (J. N. Brantley et al., *Science* 2011, 333, 1606-1609). This chemical mechanism is used in this embodiment to cause changes in the fluidity and diffusivity of the therapeutic apparatus, to induce enhanced therapeutic delivery via locally-facilitated diffusion as illustrated in FIG. 8. In this particular embodiment, the use of PMA is doubly advantageous, as PMA is known for its ability to absorb many times its own mass in fluid, making it an absorbent and effective bandage/dressing material. This represents only one embodiment of both the triazole/PMA-based mechanical bond cleavage approach, as well as only one therapeutic apparatus degradation approach. Many other approaches are possible which fall within the scope of the invention, including alternative encapsulation schemes using different polymers and/or linker groups as well as other schemes in which the therapeutic is attached to the matrix polymer directly, rather than enmeshed.

Therapeutics can be released through micro- or macro-structural degradation of a therapeutic release matrix. Here, micro-structural degradation is defined as structural alterations of a matrix leading to therapeutic release at the nanometer and single micrometer size scales. Macro-structural degradation instead indicates structural alterations that occur at size scales larger than 10 micrometers. Multiple therapeutics can be packaged within in each region for the simultaneous release of a complete therapeutic regimen. Alternatively, for cases where it is not desirable or possible that the therapeutics be co-administered, different therapeutics or therapeutic regimens can be spatially patterned to different regions in the therapeutic apparatus. These different therapeutics or therapeutic regimens may be color-coded, both for indication (for example, red, blue, or green on the distal patch side) and to differentiate between different released therapeutics. For example, blue light releases a first therapeutic, and red light releases a second therapeutic. Additionally, any light actuated moiety could be used to trigger a catalytic and/or cascading sequence that leads to rapid structural degradation. Furthermore, a therapeutic can be contained in a nanoparticle form that is released from a matrix, such as a polymer, gel, or hydrogel, upon light activation via any of the mechanisms previously described.

In other embodiments of the invention, spatioselective therapeutic release is accomplished using a bandage apparatus formulated as an adhesive patch that stays affixed to a patient. A user can trigger the release of therapeutics in a controlled manner through the use of an interacting apparatus delivering light when held against the bandage apparatus. Following administration, the irradiated region of the patch can change color to indicate that therapeutic has been released. A single patch can hold a multitude of therapeutic releasing regions.

Furthermore, embodiments of the invention can be combined with therapeutic eluting patch technologies currently in use. These drug-eluting patches include single and double layer drug-in-adhesive patches as well as reservoir, matrix, and vapor patch designs. For example, single and multiple drug-in-adhesive patches could be readily used in combination with the therapeutic release matrices described here. Reservoir, matrix and vapor patch technologies can be embedded into embodiments of the invention, including, but not limited to, regions/spaces not containing light-actuated therapeutic release matrices, layers within the embodiment, or into therapeutic release apparatus itself.

As a specific example of a therapeutic apparatus, the anti-inflammatory therapeutic Diclofenac (2-(2-(2,6-dichlorophenylamino)phenyl)acetic acid) is embedded with the photoactive molecule methylene blue into a layer of PLGA adhered to the proximal surface of a plastic backing material. The patch backing material is composed of a 0.3 cm thick layer of polyvinyl alcohol. The proximal layer of the patch contains an adhesive layer composed of methylcellulose gel. The therapeutic releasing polymer matrix is patterned over the patch proximal surface in 1 cm diameter circular regions each separated by 2 cm. Each circular region has a corresponding circle that appears on the distal patch surface to indicate the exact spatial location of the therapeutic releasing apparatus in the patch. In this example, the spatial location is marked with cis-azobenzene, which undergoes trans isomerization when illuminated with 635 nanometer light that results in a color change post-irradiation. This color change indicates that a specific region of the patch has been used.

It should be noted that the use of light in many of these embodiments can be replaced with mechanical disruption through pressure from an external source. For example, the therapeutic release matrix could be a bladder filled with a single or multiple therapeutics that is released upon its rupture. The flow of material from the bladder would facilitate delivery of the therapeutic(s) to the patient. In another embodiment, the use of pressure could trigger a material to structurally expand, leading to the release of therapeutic.

In one embodiment of the invention, the interacting apparatus can take the shape of a hand-held device, such as a pen-shaped applicator, that can hold an internal power supply such as a battery. For use with light-based therapeutic release matrices, this power supply powers a bright light emitting diode (LED) affixed to one end. The LED would be selected to emit a specific color of light, for example red light at, for example, approximately 630 nanometers. This LED can be switched on through the press of a button on the pen or activated by pressing the interacting apparatus against a surface. Once activated, the LED would remain operational for a set period of time determined by an electronic circuit inside the pen. In the case of a pressure-induced therapeutic release apparatus, an ultrasonic emitter can be powered by the power source, turned on by the user, and controlled using an electronic circuit. An electronic circuit used with an energy device such as an LED or ultrasound emitter can interface with a computer, mobile platform, or network to receive programming instructions, including information regarding total administrative dose, and number of doses within a set period of time. This electronic circuit could also interface with the computer, mobile platform, or network to communicate treatment information including number of times used, number of doses received, the historical dose schedule, and the like. The electronic circuit can either contain a data storage mechanism, or can interface with a computer, mobile platform, or network to store the information.

One embodiment of the invention is designed for use on patients with open wounds and is comprised of diagnostic (sensing), treatment (therapeutic), and interacting apparatuses. It is known in the art that regions of local inflammation in acute and chronic wounds display high relative oxygen levels in contrast to non-inflamed tissue. An embodiment of the invention that reports tissue oxygenation could be used to identify and spatially map regions of inflammation in wounds, providing detailed wound status information to a caregiver or physician. Once these specific sites of inflammation are recognized, they can be treated using the interactive technology in the invention through user-triggered release of anti-inflammatory therapeutics using the interacting apparatus.

Once therapeutics have been delivered, the oxygenation status of the wound can be monitored to follow the inflammation status of regions treated, either using the interacting apparatus or other recording devices, to provide real-time therapeutic response feedback. A caregiver or physician treating the wound using this invention could then use the displayed information to determine the next optimal course of treatment, all without removing the invention and compromising sterility.

The applicants' research has led to the development of rapid-feedback molecular probes that measure tissue parameters such as oxygen concentration (also called oxygen tension).

Figure 9:
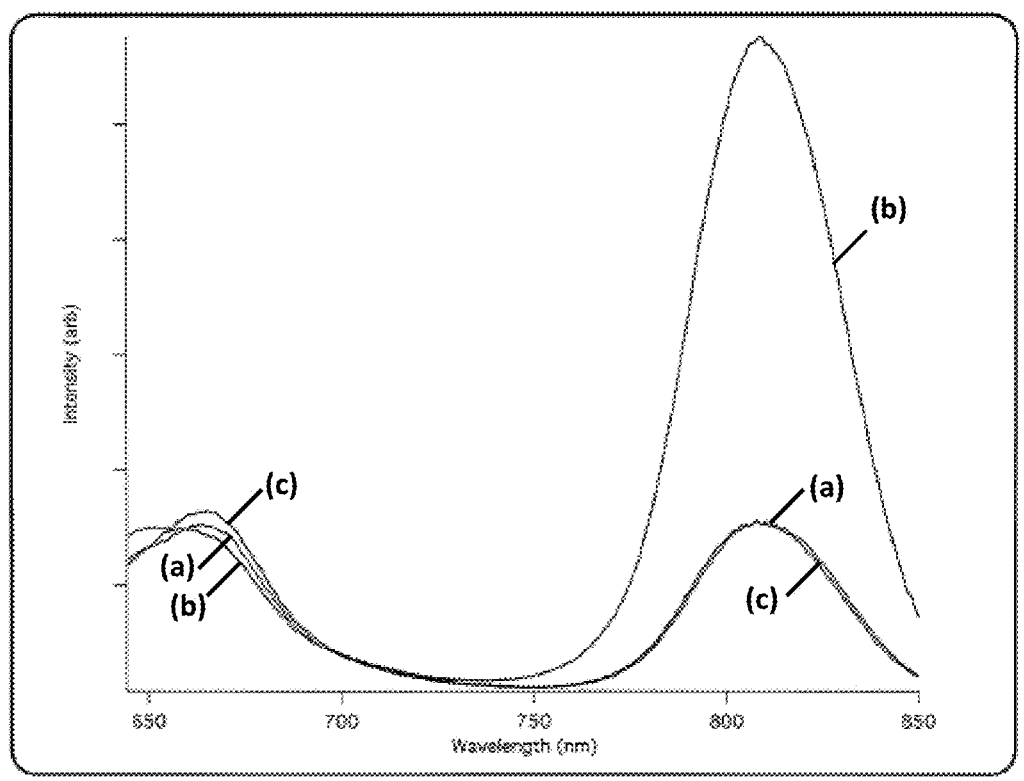
FIG. 9 is a graph showing the spectral response of an oxygen sensor element in accordance with the present invention when illuminated with 635 nanometer light under different atmospheric conditions.
Figure 10A:
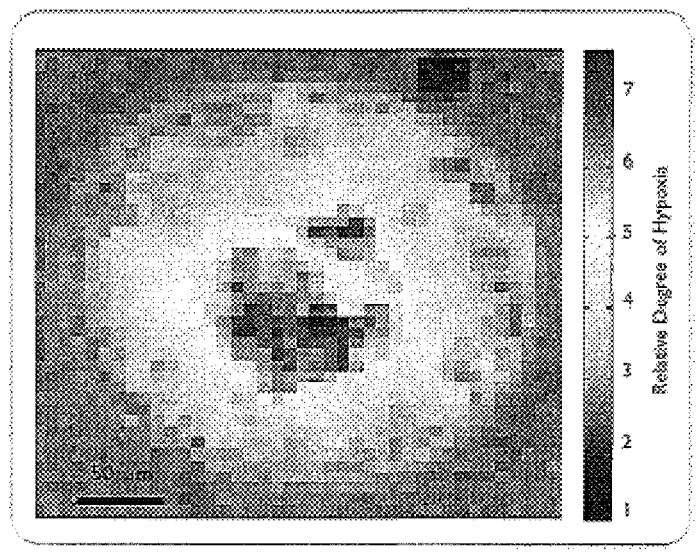
FIG. 10A is a spatial mapping of oxygen tension in a model ovarian tumor in vitro.
Figure 10B:
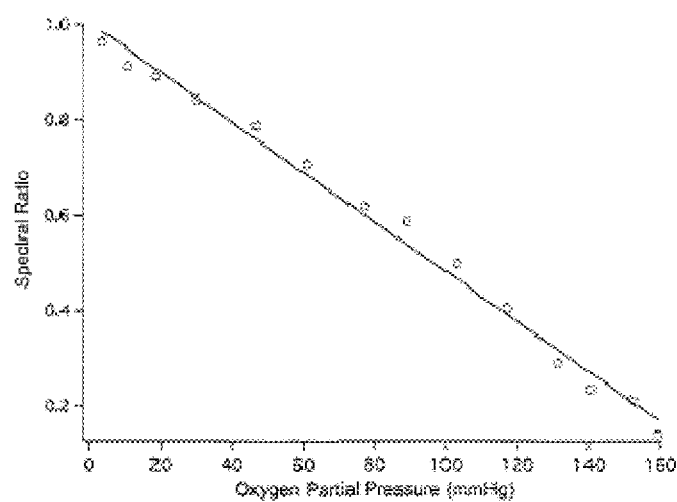
FIG. 10B is a graph showing the calibrated spectral ratio as a function of oxygen tension. This calibrated ratio can be used for spatial mapping of oxygen tension in biological systems, such as a model ovarian tumor in vitro shown in FIG. 10A.

These oxygen reporting systems can utilize molecules (that is, fluorophores) whose emission properties are insensitive to oxygen along with molecules (that is, phosphors) whose emission properties are influenced by molecular oxygen concentration. As illustrated in FIG. 9, emission from the fluorophore/phosphor probe can be used to measure oxygen tension in biological systems reversibly with high fidelity. A first curve (a) shows an initial emission spectrum from the probe in air, while a second curve (b) shows emission following equilibration of the probe in a substantially oxygen free environment (i.e., following a nitrogen purge). Finally, a third curve (c) shows emission after once again equilibrating the probe in air. As expected, curves (a) and (c) display a similar profile. Such probes can be calibrated so that the spectral ratio between fluorophore and phosphor emission correlate with oxygen concentration. Furthermore, this calibration can be used to read out a map of oxygen concentration in biological samples as shown in FIGS. 10A-B. It is also possible to utilize molecules such as dyes whose light absorption properties (such as, absorption wavelength or absorption cross-section) can be modulated by the presence of analytes such as oxygen for light absorption-based colorimetric oxygen measurements.

The present invention provides a system and method for imaging of multiple tissue parameters using a wound dressing. The invention provided here allows the selective, local release of therapeutics (as described previously and further detailed below) to any part of the tissue or wound covered by the dressing, as well as the subsequent monitoring of physiological parameters to assess therapeutic response.

Figure 11:
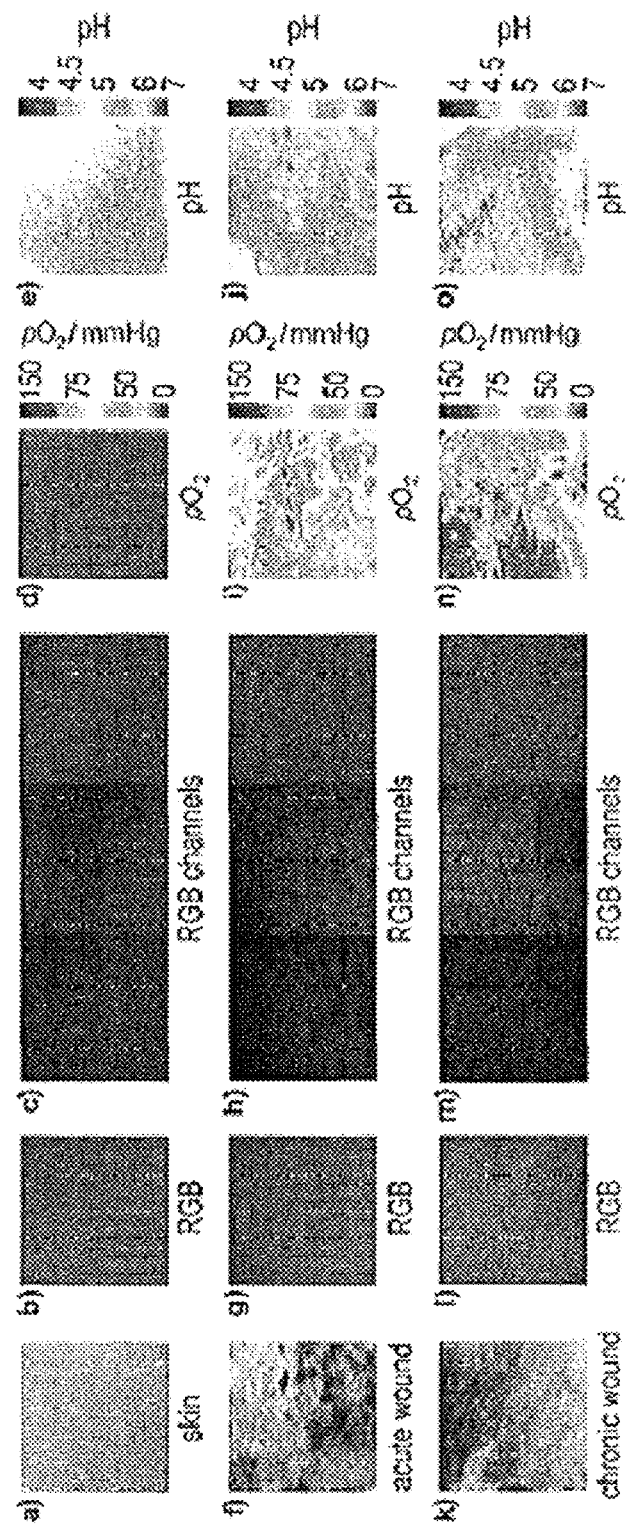
FIG. 11 provides a series of reports related to an in vivo application of the dual $O_2$/pH sensor on a plain skin surface (a-e), a skin graft donor site as a model for acute wound healing (f-j), and a chronic wound (k-o). Imaging of $pO_2$ and pH on intact skin (d and e, respectively) showed homogeneous distribution, while heterogeneity was observed in the case of a chronic wound imaging (n and o respectively), as reported in Meier et al., *Angewandte Chemie International Edition,* 50(46): 10893-10896, 2011.

The feasibility of imaging tissue parameters (namely $pO_2$ and pH) using a conventional digital camera, has been demonstrated. The device displayed a wavelength dependent readout, with the data being stored in 3-color (red/green/blue) RGB channels. Referring to FIG. 11, sensing elements were encapsulated in an analyte-permeable membrane, to form a skin patch for wound healing monitoring. The method was applied on intact skin as well as on a chronic wound. In the case of intact skin imaging, a homogeneous distribution of $pO_2$ and pH was observed. On the other hand, oxygen and pH values of a chronic wound indicated a sustained inflammatory phase.

Figure 12:
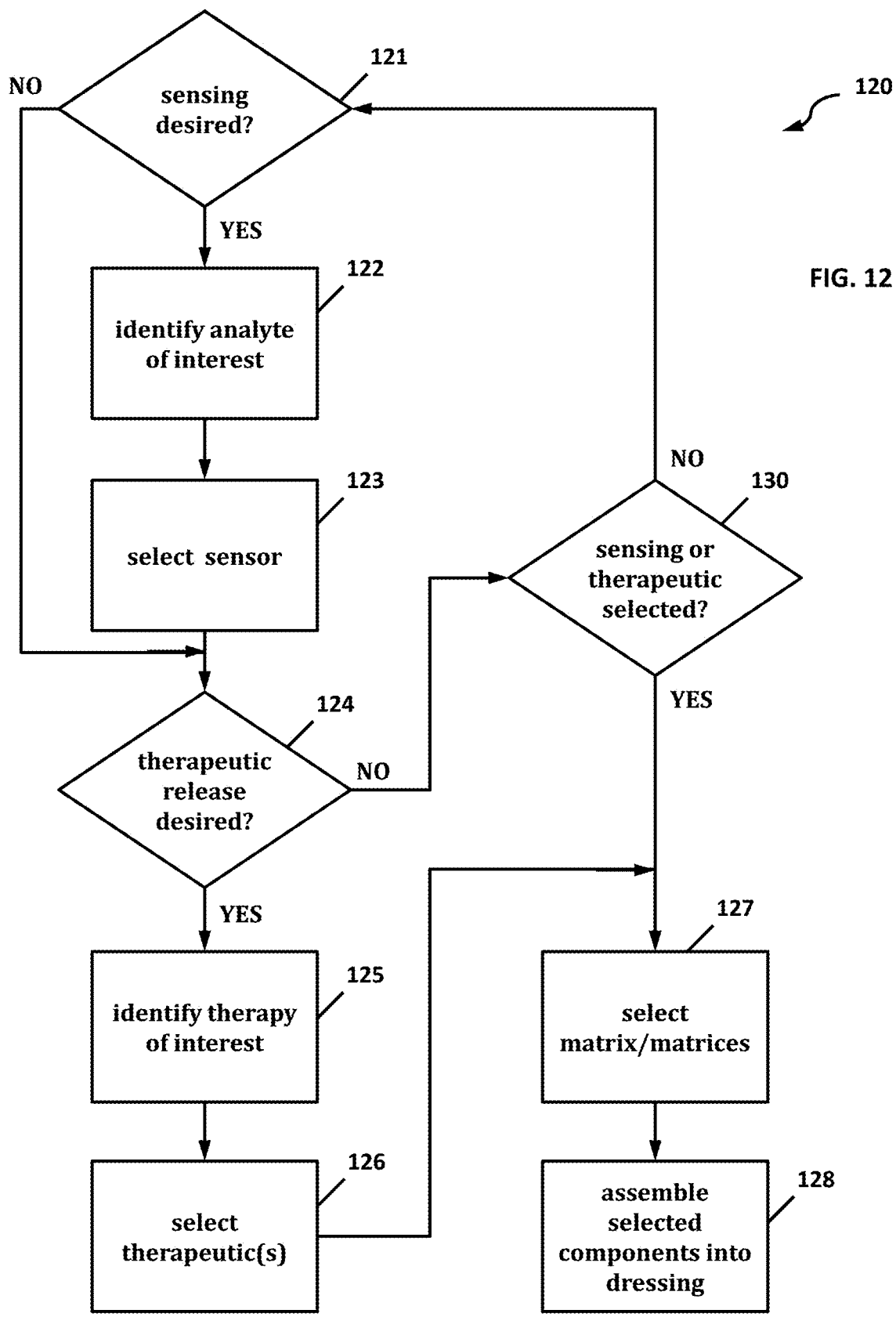
FIG. 12 is a flowchart illustrating an embodiment of a method for manufacturing a device of the present invention.

Turning now to FIG. 12, a flowchart is provided to illustrate a method 120 for manufacturing a device of the present invention. The exemplary method 120 includes, in step 121, a manufacturer or a physician determining whether it is desirable that a given device includes a sensing portion. If the individual determines that a sensing component is desired, in a next step 122, the individual identifies an analyte of interest to be sensed by the sensing portion. Once an analyte has been identified, in step 123, a sensor suitable for detecting the identified analyte is selected. For example, if molecular oxygen is the analyte of interest, a meso-unsubstituted metallated porphyrin molecule designed to be an effective sensor for oxygen may be selected. The porphyrin molecule can be excited with a specific wavelength of light and the presence of oxygen can be detected by measuring a corresponding phosphorescent emission signal.

Having selected a sensor, in step 124, the designer determines whether or not a therapeutic portion is desired. If a therapeutic portion is to be included, a therapy of interest is identified in step 125. The identified therapy may include the release of pain medication such as an NSAID. Based on the therapy identified in step 125, the therapeutic(s), such as one or more NSAIDs is selected in step 126.

The selection of a therapeutic portion can be done to ensure the compatibility of the sensor with the matrix, such as will be described below. That is, selection of a therapeutic portion may be done with consideration to the compatibility of the sensor and, as will be described, the matrix, such that selection of the therapeutic portion is based on a chemical property of one or both of the sensor and the matrix.

For example, one embodiment involves combining a singlet-oxygen degradable polymer, which can be the basic component of the therapeutic release matrix, with an oxygen-independent, free-base porphyrin core that could generate enough singlet oxygen to trigger the matrix degradation. A metallated, dendritic analogue of that porphyrin serves as the oxygen-reporting molecule, and is embedded in the sensing matrix selected at step 123. Having inherently different properties, these two molecules can be actuated using light of different wavelengths; thus allowing on-demand control of oxygen sensing separate from therapeutic release. Moreover, dendritic encapsulation can efficiently minimize the amount of singlet oxygen that can reach the therapeutic matrix following light-activation of the oxygen-reporting molecule, thus maximizing selectivity in the use of the free-base porphyrin (or any photosensitizer) for light-activated therapeutic release.

In step 127, given the selected components, a suitable matrix material is selected. As described previously, individual matrix materials can be selected for each of the sensing and therapeutic portions or a single matrix may be selected to support both of the sensing and therapeutic portions.

In one embodiment, the sensor may be enmeshed in the matrix material. Mixing of the sensing matrix components with the sensor may involve the use an additional, silyl-based component (Triisopropylsilyl chloride or TIPS-Cl) that is similar in structure with those found in the mixture that forms the matrix (Polydimethylsiloxane or PDMS). For a given formulation technique to improve the compatibility of the sensor with the matrix material, the oxygen-reporting molecule of the sensor may be enmeshed within the matrix. Specifically, to achieve a desired enmeshing, a matrix base may be selected based on a chemical nature of the sensor, such that the matrix base is ensured to be desirably compatible with the sensor and ensures "curing."

The compatibility between the sensor and its matrix is highly dependent on the structural similarity between the two components. For example, the compatibility may be dependent upon hydrophobicity, polarity of surface functional groups, polarity of the entire molecule, type and number of charges, molecular weight, stability, reactivity, and other factors.

For example, sensor molecules modified with glutamic dendrimers carry highly polar surface functional groups, which is not compatible with the low-polarity hydrophobic PDMS matrix. If the sensor molecules were mixed into the PDMS curing mixture as a dichloromethane (DCM) solution, they would agglomerate and precipitate out of the curing mixture. When dimethylformamide (DMF) is used as the solvent for the sensor molecules, better mixing can be achieved with the curing mixture. However, the curing mixture does not polymerize and form a solid bandage in the presence of DMF. In accordance with one aspect of the present invention, triisopropylsilyl chloride (TIPS-Cl) can be added as a polar, yet hydrophobic, co-solvent to facilitate the mixing of the sensor molecules and PDMS. It is also structurally similar to the components of the PDMS curing mixture and, therefore, does not interfere with the curing process.

Therefore, some general factors that may be considered while matching the sensor molecules with the bandage matrix include the chemical structures of the sensor and matrix, concentration of the sensor molecule inside the matrix, and potential changes in the matrix's optical, mechanical, and chemical properties upon mixing the two. In this regard, it is advantageous to select the matrix based on a chemical nature of the sensor or vice versa.

Thus, step 127 stands in contrast to other approaches for coupling a sensor with another material, such as using solvents to solubilize an oxygen-reporting molecule in the sensing matrix mixture because such attempts have been shown to be incompatible as they prevent the polymerization process known as "curing", which is the basis for forming a solid and flexible sensing matrix from a viscous mixture of different components.

Finally, in step 128, the sensing and therapeutic portions and the selected matrix materials are assembled into a device, such as a dressing. Notably, a designer can choose to omit either of the sensing and therapeutic portions. For example, in step 121, if the designer determines that a sensing portion is not desirable, method 120 indicates that the designer should proceed directly to step 124. However, it is preferable that at least one of the sensing and therapeutic portions is included. Therefore, if in step 124, it is determined that a therapeutic portion is not desired, method 120 includes a step 130 in which if neither sensing nor therapeutic was selected for inclusion in the manufacture of the dressing, the method 120 proceeds to step 121. Alternatively, if at least one of a sensing and therapeutic portion is desired, method 120 indicates that the designer should proceed to step 127.

For embodiments of the present invention that incorporate the aforementioned oxygen reporting probes, the sensing portion can include a matrix composed of a highly breathable polydimethylsiloxane (PDMS) layer where the sensing molecules are enmeshed, and a polyvinyl chloride/polyvinylidene chloride (PVC/PVDC) gas-impermeable layer to block out room oxygen. The use of alternative materials is envisioned, wherein the material is selected based on the desired permeability characteristics. Examples of such materials are described in Table 1.

TABLE 1

Oxygen Permeability of different polymeric materials ($O_2$ permeability has units of $10^{-10}$ $cm^2$ $s^{-1}$ $cmHg^{-1}$).

| Polymer | $O_2$ Permeability |
|---|---|
| Silicone (PDMS) | 76-460 |
| poly(isoprene) (natural rubber) | 23.3 |
| polyurethane (PU) | 1.1-3.6 |
| low density polyethylene (PE) | 2.2 |
| polycarbonate (PC) | 1.4 |
| poly(ethyl methacrylate) (PEMA) | 1.2 |
| high density polyethylene (PE) | 0.3 |
| poly(methyl methacrylate) (PMMA) | 0.1 |
| polyvinyl chloride (PVC) | 0.045 |
| Polytetrafluoroethylene (PTFE) | 0.04 |
| polyester (PET) | 0.02 |
| polyvinylidene chloride (PVDC) | 0.005 |

While permeability is one parameter to consider in the design and construction of a dressing in accordance with the present invention, the amount (or thickness) of the material may also be considered. For example, the commercial transparent film "Tegaderm" is mainly composed of polyurethane (PU) and acrylate polymers (for example, PMMA, PEMA). They are advertised as breathable and suitable for chronic wound dressing even through PU has a low permeability compared with PDMS.

Based on the aforementioned factors, it is possible to choose a polymeric material (included but not limited to the ones listed in Table 1) or a combination of polymers to be used as the outer layer of the embodiment that would prevent room oxygen from interfering with the sensing bandage, while maintaining enough oxygen exchange capability that is necessary for wound healing.

Additionally, it is possible to tune the gas permeability of the barrier materials to adapt to different clinical applications. Higher breathability materials can be used in chronic wound dressings designed for long-term wearing, where sufficient oxygen exchange is essential for the healing of the wounds. If the bandage is designed for acute wound management, where a quick oxygen reading and other properties of the bandage (exudate absorption, moisture keeping, infection control, and the like) are desired, less permeable materials can be used as the barrier layer.

Another aspect of the present invention relates to acute wound and burn management. Traumatic injuries result in acute wounds and burns that often require skin grafts or flaps to salvage tissue and limbs to restore function and improve cosmetic outcome. Postsurgical assessment of perfusion and oxygenation in acute wounds and burns is typically qualitative and subjective, relying on episodic assessments such as wound color and temperature, capillary refill, Doppler ultrasound and touch (Park et al., *The Surgical Clinics of North America*, 90(6): 1181-1194, 2010). These approaches require extensive training, are subject to operator experience, and can miss critical events due to their episodic nature, leading to poor surgical outcome. For example, surgical rehabilitation procedures for wounded warriors, such as reconstructive micro-surgery, can fail due to undetected anastomotic failure, causing loss of perfusion and subsequent ischemia, infarction and necrosis of the transplanted tissue (Orgill et al., *The New England Journal of Medicine*, 360(9):893-901, 2009). This is also problematic when laying skin over thermal burns, where insufficient debridement results in the inability to detect adequate graft blood supply, leading to subsequent graft failure (Meier et al., *Angewandte Chemie International Edition*, 50(46): 10893-10896, 2011). This problem of partial graft take has particularly dire consequences in the treatment of maxillofacial burns, where the loss of grafted skin has profound recovery, functional, cosmetic consequences. Current oxygen sensing technologies rely on fragile point-by-point measurement tools that are not easily integrated into surgical settings or post-treatment care.

Problematically, acute wounds and burns are often heterogeneous, with complex patterns of inflammation and infection. Inflammation in wounds and burns can lead to poor graft take, while infection can significantly complicate the grafting procedure and post-surgical recovery. Inflammation can be readily visualized in acute wounds, as inflamed tissue regions display greater baseline oxygenation (Meier et al., *Angewandte Chemie International Edition*, 50(46): 10893-10896, 2011) than healthy tissue. Infections result in the depletion of local tissue oxygen as well as changes in the wound bed pH. Spatiotargeted therapeutic interventions, such as the treatment of inflammation, currently require the removal of wound dressings to enable therapeutic application, which can cause a loss of sterility and can disrupt the wound, burn, or graft.

The invention provides a solution to these complex clinical problems. The invention can be built to display an active, real-time map of both oxygenation and pH across the entire wound or burn site for either colorimetric or augmented reality display. The oxygen and pH sensors themselves can be embedded in a bandage apparatus and separated from the wound or burn surface via selectively permeable membranes. This ensures readout of tissue properties without any risk of interaction with the bandage sensors. This readout is of great importance in the skin graft process for the treatment of burns, as the burn site must be adequately debrided for a graft to take. Inadequate debridement results in low perfusion and oxygenation that often results in graft failure. On the other hand, overdebridement can remove critical tissues layers necessary for graft take and recovery of function. A bandage apparatus capable of visualizing perfusion and oxygenation across a burn site would save numerous surgical protocols and allow physicians to better plan their interventions to maximize graft success and minimize patient impact. Equally important, a bandage apparatus that can allow for the selective, spatial administration of therapeutics will allow caregivers to treat inflammation and infection without bandage removal and the accompanying disruption of the burn and loss of sterility.

To allow for therapeutic intervention, a separate portion of the invention contains therapeutics embedded in light-degraded polymers triggered by specific wavelengths of light. An interacting apparatus containing various colored LEDs is applied to the sensing and therapeutic bandage apparatus, with a specific color LED triggering the selective release of a specific therapeutic. For example, regions of inflammation can be exposed to blue light to release an anti-inflammatory, while an infected region in the same wound sight can be treated with antibodies through red-light illumination. Thus, the invention-provided oxygenation and/or pH mapping allows for spatiotargeted delivery of needed therapeutics to affected tissue regions, without ever removing the bandage or compromising sterility. Moreover, since the invention remains on the wound, the same oxygen and pH mapping capability can track the recovery process, providing clinicians with real-time feedback for accurate wound recovery assessment.

Another aspect of the present invention relates to chronic wounds (for example, ulcers) management. Chronic wound management is a challenging healthcare problem, with an estimated 2% of the world population suffering from chronic wounds or associated co-morbidities (Gethin et al., *Wounds UK,* 3(3):52-55, 2007). Major sources of chronic wounds include venous and/or arterial ulcers, decubitus ulcers (bed/pressure sores), and diabetic ulcers. Although chronic wounds afflict patients from all demographics and age groups, the elderly and diabetics are particularly effected, accruing collective wound management costs in excess of $10 billion annually (Snyder et al., *Clinics in dermatology,* 23(4):388-95, 2005).

The present invention provides a platform that offers several applications in the management of chronic wounds. As a first example, chronic wound patients report severe, persistent pain that adversely affects their activity level and quality of life (Jorgensen et al., *Official Publication of the Wound Healing Society [and] the European Tissue Repair Society,* 14(3):233-9, 2006). Although a wide variety of oral pain medications are available for pain management, pain from chronic wounds such as venous leg ulcers is often undertreated due to patient frailty, contraindication or poor tolerance of systemic analgesics, or simple reluctance to take more medicine. These patients also report severe pain associated with frequent bandage changes (Jorgensen et al., *Official Publication of the Wound Healing Society [and] the European Tissue Repair Society,* 14(3):233-9, 2006). Additionally, the World Health Organization (WHO) guidelines for pain management suggest following a "pain relief ladder," starting from the lowest level (that is, non-narcotic non-steroidal anti-inflammatory-NSAIDs) and moving upwards to local and/or systemic opiates as needed. Although Jorgensen et al. recently repotted development of a NSAID-eluting foam wound dressing for treatment of venous leg ulcers, this solution offers only the lowest level of pain management (Jørgensen, Bo, et al., (2006) *Journal of Wound Repair and Regeneration,* vol. 14, iss. 3, pp. 233-239). Furthermore, the presence of a wound dressing on the wound bed precludes the possibility of further local pain management without bandage removal.

An embodiment of the invention can function as a tiered chronic wound pain management platform, offering the ability to treat pain on-demand spatiospecifically. In one embodiment of the invention, the therapeutic apparatus within a bandage apparatus contains NSAIDs, which can either be constitutively eluted or eluted in response to a particular wavelength of light administered by the interacting apparatus (for example, green light). In this same embodiment, the therapeutic apparatus also contains an additional drug, representing a "step up" on the WHO pain ladder (for example, fentanyl, buprenorphine, or morphine), that is eluted from the therapeutic apparatus in response to a different wavelength of light (for example, blue light). Thus, patients or caregivers could avoid unnecessary consumption of opiate therapeutics, relying instead on spatiospecific therapeutic administration on an as-needed basis.

Additionally, the frequency of dressing removal and wound examination can be further reduced by the invention's capacity as a spatiospecific sensor of physiologically relevant parameters, such as pH. It is known in the art that pH can be correlated to the clinical stage of pressure ulcers (Gethin et al., *Wounds UK,* 3(3):52-55, 2007) and could therefore be used to monitor wound healing as well as identify potential problems, such as infection, without the painful, labor-intensive, and psychologically problematic process of repeated dressing removal. Furthermore, early identification of wound regression would accelerate identification of wound pathologies, intervention, and treatment, thereby potentially preventing co-morbidities such as infection. pH also has been shown to correlate to oxygen tension, itself an important indicator of wound healing.

A specially-tailored bandage apparatus can be additionally used to monitor and display lipopolysaccharides (LPS) as an indication of infections and release antibiotics on-demand. Moreover, the management and surgery of chronic wounds is similar to what is found in the treatment of burn grafts. Thus embodiments of the invention could be used in a similar fashion to verify adequate debridement and monitor wound beds post-operatively for infection without bandage removal.

Another aspect of the present invention relates to pain management. The invention can be used to avoid the use of needles, catheters, infusion and syringe pumps while the associated interacting apparatus would allow remote telemetry and monitoring. Therefore, pain medication could be customized and calibrated in real-time to patient's pain intensity as measured by the pain scale. Accurate dosimetry and calibration has the potential of decreasing side effects.

Another aspect of the present invention relates to accelerated on-demand therapeutic delivery. Many currently used therapeutic delivery patches and bandages use reservoirs saturated with a given drug that is separated from the patient's skin by a membrane. For this type of patch, the membrane is chosen such that the rate of therapeutic diffusion through the membrane is lower than that of the protective skin layer called the stratum corneum. This ensures that the elution of the therapeutic through the membrane occurs at a rate allowing for transdermal delivery. Less expensive designs incorporate adhesive layers that accomplish the same effect, where the adhesive acts as both a reservoir and a diffusion-controlling matrix (Prausnitz et al., *Nature biotechnology,* 26(11): 1261-8, November 2008).

The key limitation of these approaches is that the delivery rate of the therapeutic is ultimately bound by the transdermal therapeutic transport rate. This can be acceptable for slow-therapeutic release systems or for marginally hydrophilic therapeutics. However, most existing drugs are significantly hydrophobic, and in many cases need to be delivered in a single dose instead of extended timed release. Also problematic is that patches based on diffusion are environmentally sensitive: fentanyl patches accidentally worn in a hot shower, for example, lead to patient deaths due to increased diffusion at higher temperatures.

A solution to these issues would be a mechanism that could temporarily disrupt the stratum corneum to facilitate increased therapeutic diffusion. One proposed mechanism would be to disrupt the stratum corneum using photodynamic therapy (Dougherty et al., *Journal of the National Cancer Institute,* 90(12):889-905, 1998). In this approach, a hydrophobic photosensitizer with limited dermal penetration would be taken up by the stratum corneum. Under illumination, reactive radical species released by the photosensitizer would react, opening up pores and fissures in the stratum corneum through which therapeutics could travel. Short-wavelength, blue light could additionally be used for photoactivation to limit the depth of reactive radical specie generation to only the stratum corneum.

Following disruption of the stratum corneum, therapeutics in the invention could either (1) directly then flow into the tissue, (2) be released through a semi-permeable membrane, or (3) be triggered for release via a secondary membrane containing a different photosensitizer. The first case, direct flow of therapeutics, would be useful for short-term, instant release of therapeutic agents not compatible with existing transdermal approaches. This case would also be useful for the delivery of therapeutics in special populations, such as children or the elderly, where standard administration approaches are either difficult or impossible to use.

Release through a semi-permeable membrane could be used to build embodiments of the invention with a selective "on" mechanism. Without the photodynamic action to facilitate local breakdown of the stratum corneum, patch and bandage embodiments of the invention would remain entirely dormant. Only illumination with light would enable the release of therapeutic agents. This approach could be of use in situations that require self dosing, such as home-care, or be used for low-cost, third world applications where sunlight can be used to activate patch and/or bandage embodiments of the invention.

Another aspect of the present invention relates to vaccine delivery. The need for safe and efficient vaccine administration depends on engineering simple tools for transdermal delivery. One challenges to overcome is the limited penetration of materials through the stratum corneum. A number of different techniques that facilitate transcutaneous drug delivery are known in the art. Such drug delivery methods disrupt the stratum corneum, for example, through the use of microneedles (Bariya et al., *Journal of Pharmacy and Pharmacology*, 64(1):11-29, 2012; Vrdoljak et al., *Journal of Controlled Release*, 159(1):34-42, 2012) and ablative fractional lasers (AFL) (Chen et al., *Journal of Controlled Release*, 159(1):43-51, 2012), which are minimally invasive and not entirely painless, and/or require skin pretreatment.

Skin patches for transcutaneous vaccine delivery offer the advantages of being a noninvasive, painless and cost-effective method of immunization that does not require the assistance of highly trained health care personnel. In one example, a hydrogel patch is used in transcutaneous vaccination for tetanus and diphtheria (Hirobe et al., *Vaccine*, 30(10): 1847-1854, 2012). Octyldodecyllactate, which is an absorption enhancer that disrupts the lipid bilayer of the stratum corneum (Hood et al., *Food and Chemical Toxicology*, 37(11): 1105-1111, 1999), was used in the preparation of the patch in order to promote the transmission of the vaccines through the skin. Embodiments of the invention that make use of light-activated skin penetration enhancement, as discussed above, could allow for the release of a vaccine from a skin patch apparatus for the controlled release of vaccine doses. In one embodiment of the invention, this could be achieved with polymer cages encapsulating vaccines that are degraded by applying light of a specific wavelength. Vaccine release occurs either simultaneously, or following light-activated skin penetration by using polymeric matrices with different degradation pathways.

Vaccine administration using this embodiment of the invention is applicable in areas such as pediatrics, where having a painless method that requires minimal pretreatment is essential when dealing with young patients. Moreover, it can help fight the problem of disease outbreaks in developing countries, as a simple and inexpensive way to rapidly vaccinate large populations without the need of trained healthcare personnel. In this case, light-degradable polymeric matrices that are activatable by sunlight can be used, and vaccination can be simply accomplished by exposure to sunlight.

Many additional applications exist, including but not limited to (i) pain therapeutics for palliative and chronic care, both in hospital settings and for home care; (ii) localized and spatiospecific administration of steroidal anti-inflammatory to patients suffering from chronic inflammation, sports-related injuries, or rheumatoid arthritis; (iii) antibiotics and/or anti-inflammatory therapeutics in COPD patients for use in ICUs; (iv) therapeutic administration customized for select patient populations such as pediatric, neonate, or geriatric patients; and (v) automated, remote administration of a therapeutic or therapeutics to patients in locations where medical care and/or self-administration is not an option (i.e., fighter or commercial jet pilots, unconscious/incapacitated soldiers on the battlefield, and the like).

It is therefore an advantage of the present invention to promote new areas of investigation in the fields of pain release (postoperative, acute, chronic, and palliative) and vaccination (preventive, curative). Another advantage of the present invention is to provide customized therapeutic approaches in pediatric medicine, geriatrics, and post-trauma care. Yet another advantage of the present invention is contribute to the establishment of clinically powerful and user-friendly home care and telemonitoring programs.

The invention is further illustrated in the following Examples, which are presented for purposes of illustration and not of limitation.

EXAMPLES

Example 1

Figure 13:
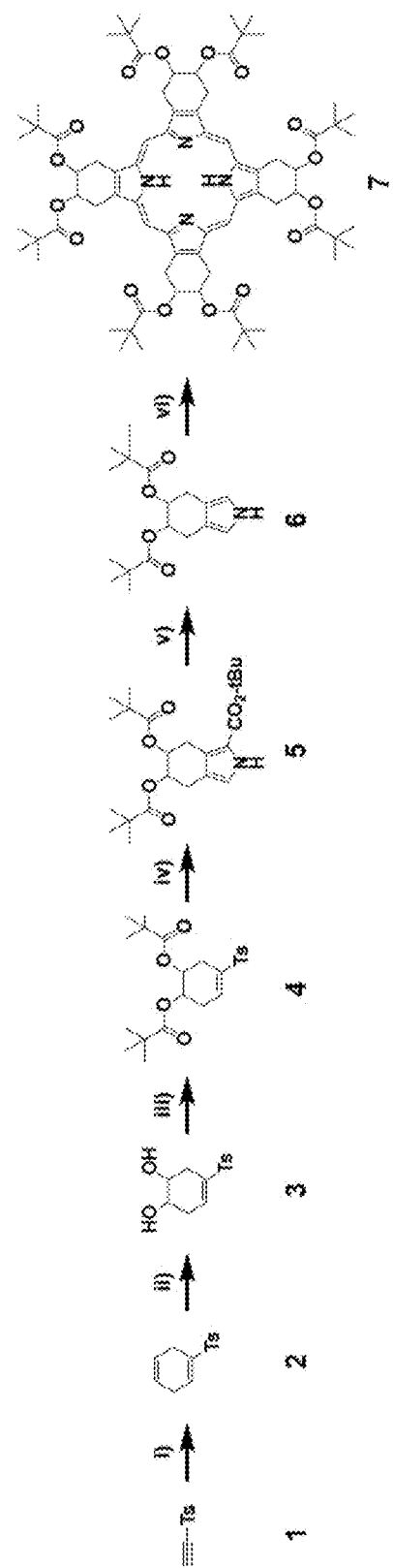
FIG. 13 shows a scheme for the synthesis of a 2,2-dimethylpropanoate functionalized, meso-unsubstituted tetracyclohexenoporphyrin.

Turning now to FIG. 13, a Scheme for the synthesis of a 2,2-dimethylpropanoate functionalized, meso-unsubstituted tetracyclohexenoporphyrin 7 is shown. The reagents and conditions labelled in FIG. 13 can be abbreviated as follows: i) 1,3-butadiene (excess), r.t., 2d, 90%; ii) $K_2OsO_4$, $K_3Fe(CN)_6$, $K_2CO_3$, $CH_3SO_2NH_2$, tBuOH/$H_2O$ (1/1), r.t., overnight, 95%; iii) $(CH_3)_3CCOCl$, 4-Dimethylaminopyridine, pyridine, $CH_2Cl_2$, r.t., overnight, 75-80% conversion; iv) $CNCH_2CO_2tBu$, tBuOK, THF, r.t., 4 h, 81%; v) TFA, r.t. 30 min, 52%; vi) p-TsOH(monohydr.), formaldehyde (37% in water), benzene, reflux (Dean-Stark condenser), 8 h, 42%.

Ethynyl p-tolyl sulfone 1 was reacted with an excess of 1,3-butadiene at room temperature for two days to form 1-(cyclohexa-1,4-dien-1-ylsulfonyl)-4-methylbenzene 2 at 90% yield. The cyclohexadienyl p-tolyl sulfone 2 was reacted with $K_2OsO_4$, $K_3Fe(CN)_6$, $K_2CO_3$, $CH_3SO_2NH_2$, tBuOH/$H_2O$ (1/1) at room temperature, overnight to form 4-tosylcyclohex-4-ene-1,2-diol 3 at 95% yield. The diol 3 was reacted with $(CH_3)_3CCOCl$, 4-Dimethylaminopyridine, pyridine, $CH_2Cl_2$ at room temperature overnight to yield a 75-80% conversion to 4-tosylcyclohex-4-ene-1,2-diyl bis(2,2-dimethylpropanoate) 4. The substituted cyclohexene 4 was reacted with $CNCH_2CO_2tBu$, tBuOK, THF at room temperature for 4 hours to form the t-butoxycarbonyl substituted, 2,2-dimethylpropanoate functionalized 4,5,6,7-tetrahydro-2H-isoindole 5 at 80% yield. The tetrahydro-2H-isoindole 5 was reacted with trifluoroacetic acid at room temperature for 30 minutes to form 4,5,6,7-tetrahydro-2H- isoindole-5,6-diyl bis(2,2-dimethylpropanoate) 6 at 52% yield. The tetrahydro-2H-isoindole 6 was condensed using p-TsOH (monohydrate), formaldehyde (37% in water), benzene, reflux (Dean-Stark condenser) for 8 hours to form 2,2-dimethylpropanoate functionalized, meso-unsubstituted tetracyclohexenoporphyrin 7 in 42% yield.

Example 2

Figure 14:
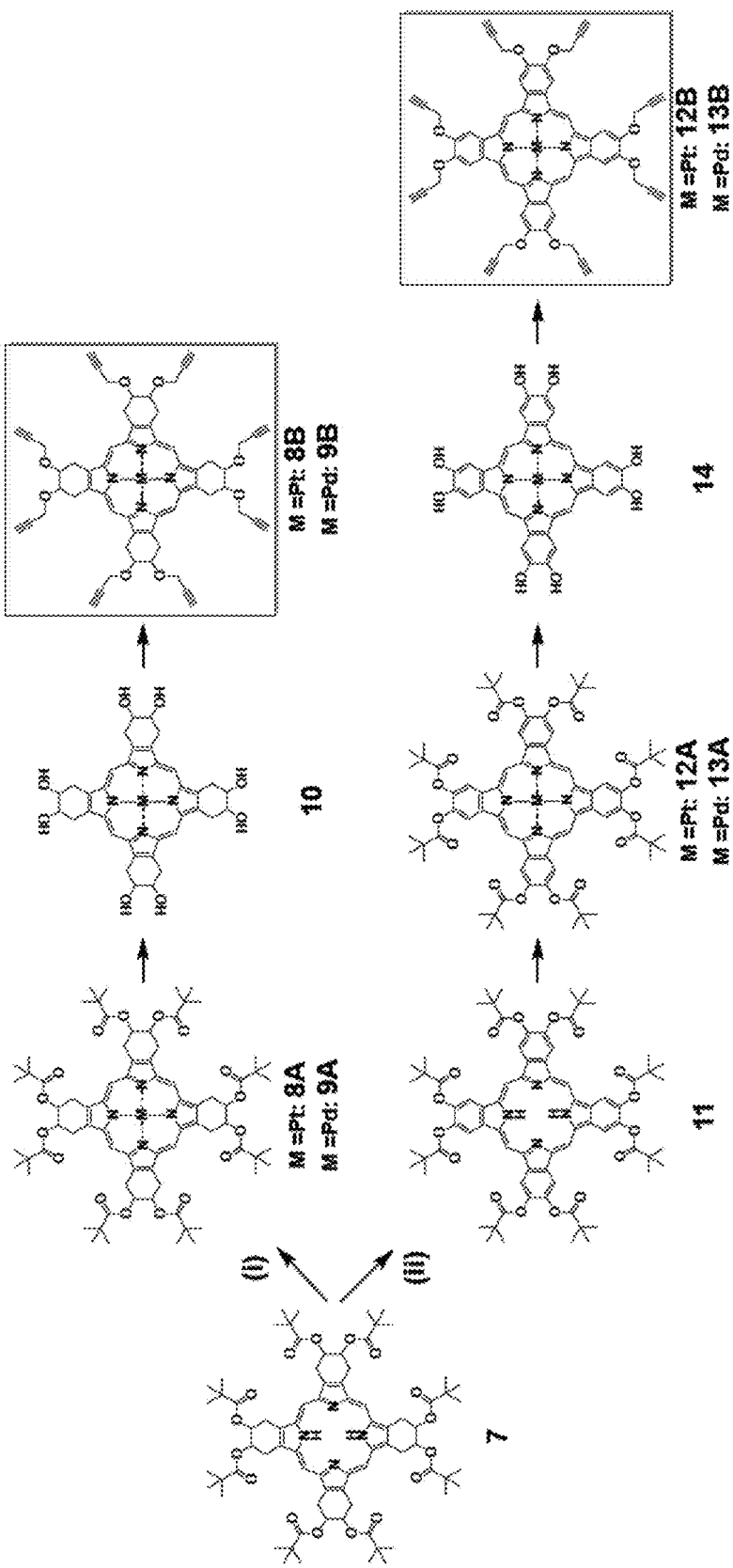
FIG. 14 shows schemes for the synthesis of (i) metallated propynyloxy functionalized, meso-unsubstituted tetracyclohexenoporphyrins, and (ii) metallated propynyloxy functionalized, meso-unsubstituted tetrabenzoporphyrins.

Turning now to FIG. 14, Schemes for the synthesis of (i) metallated propynyloxy functionalized, meso-unsubstituted tetracyclohexenoporphyrins 8B, 9B and (ii) metallated propynyloxy functionalized, meso-unsubstituted tetrabenzoporphyrins 12B, 13B are shown.

In (i), the 2,2-dimethylpropanoate functionalized, meso-unsubstituted tetracyclohexenoporphyrin 7 from FIG. 13 was refluxed with platinum chloride or palladium chloride to obtain a 2,2-dimethylpropanoate functionalized, meso-unsubstituted tetracyclohexenoporphyrin platinum complex 8A or a 2,2-dimethylpropanoate functionalized, meso-unsubstituted tetracyclohexenoporphyrin palladium complex 9A. The 2,2-dimethylpropanoate functionalized, meso-unsubstituted tetracyclohexenoporphyrin platinum complex 8A and the 2,2-dimethylpropanoate functionalized, meso-unsubstituted tetracyclohexenoporphyrin palladium complex 9A were reacted with lithium aluminum hydride in a mixture of dry dichloromethane and THF, at room temperature for 4 hours, to form the corresponding octa-hydroxy, meso-unsubstituted tetracyclohexenoporphyrin complexes 10. The octa-hydroxy, meso-unsubstituted tetracyclohexenoporphyrin complexes 10 were reacted with sodium hydride and propargyl bromide in dry N,N-Dimethylformamide, at room temperature overnight, to form the corresponding octa-propyloxy functionalized, meso-unsubstituted tetracyclohexenoporphyrin platinum complex 8B and the octa-propyloxy functionalized, meso-unsubstituted tetracyclohexenoporphyrin palladium complex 9B.

In (ii), the 2,2-dimethylpropanoate functionalized, meso-unsubstituted tetracyclohexenoporphyrin 7 from FIG. 13 was oxidized with 2,3-Dichloro-5,6-dicyano-1,4-benzoquinone (DDQ) to obtain the 2,2-dimethylpropanoate functionalized, meso-unsubstituted tetrabenzoporphyrin 11 which was refluxed with platinum chloride or palladium chloride to obtain a 2,2-dimethylpropanoate functionalized, meso-unsubstituted tetrabenzoporphyrin platinum complex 12A or a 2,2-dimethylpropanoate functionalized, meso-unsubstituted tetrabenzoporphyrin palladium complex 13A. The 2,2-dimethylpropanoate functionalized, meso-unsubstituted tetrabenzoporphyrin platinum complex 12A and the 2,2-dimethylpropanoate functionalized, meso-unsubstituted tetrabenzoporphyrin palladium complex 13A were reacted with lithium aluminum hydride in a mixture of dry dichloromethane and THF, at room temperature for 4 hours, to form the corresponding octa-hydroxy, meso-unsubstituted tetrabenzoporphyrin complexes 14. The octa-hydroxy, meso-unsubstituted tetrabenzoporphyrin complexes 14 were reacted with sodium hydride and propargyl bromide in dry N,N-Dimethylformamide, at room temperature overnight, to form the corresponding octa-propyloxy functionalized, meso-unsubstituted tetrabenzoporphyrin platinum complex 12B and the octa-propyloxy functionalized, meso-unsubstituted tetrabenzoporphyrin palladium complex 13B.

Example 3

Figure 15:
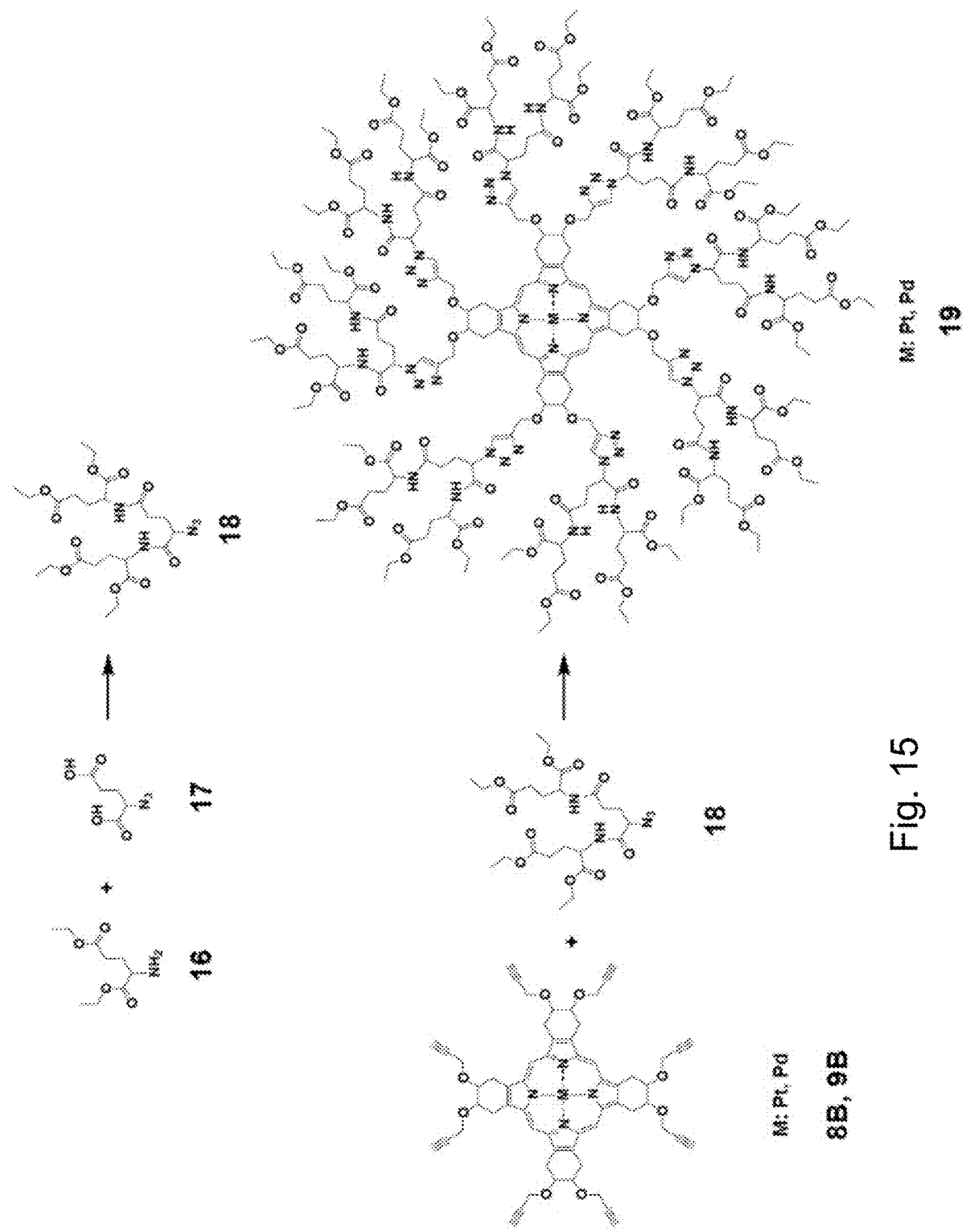
FIG. 15 shows schemes for assembling the octa-functionalized, meso-unsubstituted metallated tetracyclohexenoporphyrin-based dendrimer of FIG. 2D.

Turning now to FIG. 15, Schemes for the synthesis of an octasubstituted, meso-unsubstituted tetracyclohexenoporphyrin metal complex 19 (also shown in FIG. 2D) are shown. First, a generation-2 glutamic dendron was assembled using functionalized glutamic acid monomers (top of FIG. 15), and then the generation-2 glutamic dendron was reacted with the alkyne-terminated porphyrin core in a single step (bottom of FIG. 15) using a quick and efficient copper-catalyzed reaction known as Huisgen 1,3-dipolar cycloaddition. The reaction occurred between the alkyne groups on the porphyrin and the azide groups on the glutamate dendron.

Still referring to FIG. 15, a diethyl glutamate (diethyl 2-aminopentanedioate) 16 was reacted with the dicarboxylic acid propyl azide 17 to form the azide 18, a generation-2 glutamic dendron. The octa-propyloxy functionalized, meso-unsubstituted tetracyclohexenoporphyrin platinum complex 8B and the octa-propyloxy functionalized, meso-unsubstituted tetracyclohexenoporphyrin palladium complex 9B were reacted with the azide 18 to form the octasubstituted, meso-unsubstituted tetracyclohexenoporphyrin metal complexes 19, the platinum containing version of which can be excited when illuminated at a wavelength of 532 nanometers, followed by emission of phosphorescence at a wavelength of 644 nanometers. For the palladium containing version, the corresponding excitation/emission wavelengths are 546/674 nm.

In a similar manner, the octa-propyloxy functionalized, meso-unsubstituted tetrabenzoporphyrin platinum complex 12B and the octa-propyloxy functionalized, meso-unsubstituted tetrabenzoporphyrin palladium complex 13B can be reacted with the azide 18 to form octasubstituted, meso-unsubstituted tetrabenzoporphyrin metal complexes.

Thus, the invention provides compounds useful as a sensor in a non-invasive, oxygen sensing dressing. In one form, the compounds can be meso-unsubstituted metallated porphyrins that are sensitive towards oxygen. The metallated porphyrins can be excited when illuminated at a first wavelength, followed by emission of phosphorescence at a second wavelength whose intensity can be used as an indicator for oxygen concentration.

Although the present invention has been described in detail with reference to certain embodiments, one skilled in the art will appreciate that the present invention can be practiced by other than the described embodiments, which have been presented for purposes of illustration and not of limitation. Therefore, the scope of the appended claims should not be limited to the description of the embodiments contained herein.

The invention claimed is:

1. A method for making a porphyrin, the method comprising:
(a) condensing a compound of formula (III) with an aldehyde to form a tetracyclohexenoporphyrin ring,

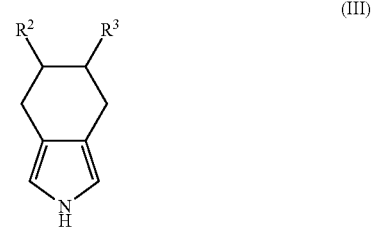

(III)

wherein $R^2$ is an atom or a group of atoms,
wherein $R^3$ is an atom or a group of atoms, and
wherein at least one of $R^2$ and $R^3$ is —$OR^4$, wherein $R^4$ is an atom or a group of atoms;

(b) metallating the tetracyclohexenoporphyrin ring to obtain a metallated tetracyclohexenoporphyrin ring;

(c) reacting the metallated tetracyclohexenoporphyrin ring with a substituted alkyne to form a phosphorescent meso-unsubstituted porphyrin having formula (I):

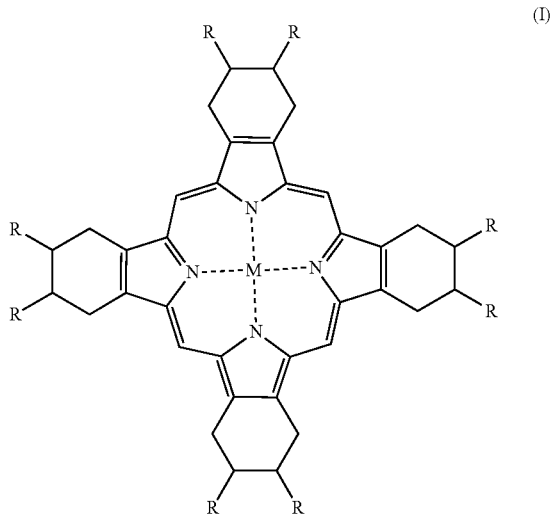

wherein M is a metal, wherein each R is independently an atom or a group of atoms, and wherein at least one R is —$OR^1$, wherein $R^1$ is alkynyl.

2. The method of claim 1 wherein:
$R^4$ is selected from the group consisting of hydrogen, substituted or unsubstituted alkyl carbonyl, substituted or unsubstituted alkyl, substituted or unsubstituted alkenyl, substituted or unsubstituted alkynyl, substituted or unsubstituted cycloalkyl, substituted or unsubstituted heterocycloalkyl, substituted or unsubstituted aryl and heteroaryl.

3. The method of claim 1 wherein:
$R^2$ is —$OR^4$, and
$R^3$ is —$OR^4$.

4. The method of claim 3 wherein:
$R^4$ is alkyl carbonyl.

5. The method of claim 3 wherein:
$R^4$ is $C_1$-$C_{10}$ alkyl carbonyl.

6. The method of claim 3 wherein:
$R^4$ is tert-butyl carbonyl.

7. The method of claim 1 wherein:
a plurality of R are —$OR^1$.

8. The method of claim 1 wherein:
every R is —$OR^1$.

9. The method of claim 1 wherein:
every R is —$OR^1$, and
$R^1$ is propynyl.

10. The method of claim 1 wherein M is platinum.

11. The method of claim 1 wherein M is palladium.

* * * * *